United States Patent
Nakayama et al.

(10) Patent No.: US 8,591,782 B2
(45) Date of Patent: Nov. 26, 2013

(54) PROCESS FOR PRODUCING STENT

(75) Inventors: Yasuhide Nakayama, Toyonaka (JP); Shogo Nishi, Neyagawa (JP); Yasushi Nemoto, Yokohama (JP); Yoshihiro Okamoto, Yokohama (JP)

(73) Assignees: National Cerebral and Cardiovascular Center, Suita-Shi (JP); Japan Stent Technology Co., Ltd., Okayama-Shi (JP)

( * ) Notice: Subject to any disclaimer, the term of this patent is extended or adjusted under 35 U.S.C. 154(b) by 902 days.

(21) Appl. No.: 10/525,016

(22) PCT Filed: Aug. 20, 2003

(86) PCT No.: PCT/JP03/10496
§ 371 (c)(1),
(2), (4) Date: Jul. 25, 2005

(87) PCT Pub. No.: WO2004/022150
PCT Pub. Date: Mar. 18, 2004

(65) Prior Publication Data
US 2006/0036311 A1 Feb. 16, 2006

(30) Foreign Application Priority Data

| Aug. 23, 2002 | (JP) | 2002-243871 |
| Apr. 14, 2003 | (JP) | 2003-109167 |
| Apr. 14, 2003 | (JP) | 2003-109168 |
| Apr. 14, 2003 | (JP) | 2003-109169 |
| Jun. 13, 2003 | (JP) | 2003-169510 |
| Jul. 24, 2003 | (JP) | 2003-201201 |
| Jul. 25, 2003 | (JP) | 2003-201836 |
| Aug. 5, 2003 | (JP) | 2003-286901 |

(51) Int. Cl.
*B29C 37/02* (2006.01)

(52) U.S. Cl.
USPC ............................................ 264/156; 264/255

(58) Field of Classification Search
USPC ............. 623/1.11, 1.12, 1.13, 1.18, 1.2, 1.27, 623/1.3, 1.39, 1.48, 1.53
See application file for complete search history.

(56) References Cited

U.S. PATENT DOCUMENTS 5,569,463 A * 10/1996 Helmus et al. ................ 424/426
5,674,241 A   10/1997 Bley et al.
5,855,598 A * 1/1999 Pinchuk ........................ 623/1.13
(Continued)

FOREIGN PATENT DOCUMENTS

EP    0 808 614 A2   11/1997
JP    S57-5048       1/1982
(Continued)

OTHER PUBLICATIONS

"Current situation of balloon stent therapy—forefront of endoscope for biliopancreatic treatment"; Japan, Kanahaea Shuppan Kabushiki Kaisha, Apr. 10, 1998; p. 124-127.

*Primary Examiner* — Monica Huson
(74) *Attorney, Agent, or Firm* — Manabu Kanesaka

(57) ABSTRACT

A stent comprising a tubular stent matrix of which diameter is extendable and a flexible polymer layer covering the stent matrix. The polymer layer is closely attached to and covers the entire surface of the stent matrix. Since the flexible polymer layer closely covers the entire surface of the stent matrix not only the outer periphery of the stent matrix, the stent has no problem of causing allergic to metal, stimulus of tissues due to metal, and rust development. Since the inner periphery of the stent is a flat and smooth surface covered by the polymer layer without convexes and concaves, the formation of thrombus can be inhibited well. There is no problem of drift between the polymer layer and the stent matrix, thereby maintaining the positional relationship between the stent matrix and the polymer layer before and after the expansion of the stent.

7 Claims, 11 Drawing Sheets

(56) References Cited

U.S. PATENT DOCUMENTS

| | | | |
|---|---|---|---|
| 6,027,525 A | 2/2000 | Suh et al. | |
| 6,120,525 A * | 9/2000 | Westcott | 606/216 |
| 6,165,212 A * | 12/2000 | Dereume et al. | 623/1.13 |
| 6,214,115 B1 | 4/2001 | Taylor et al. | |
| 6,245,099 B1 * | 6/2001 | Edwin et al. | 623/1.13 |
| 6,309,413 B1 | 10/2001 | Dereume et al. | |
| 2002/0103527 A1 | 8/2002 | Kocur et al. | |

FOREIGN PATENT DOCUMENTS

| | | |
|---|---|---|
| JP | H02-174859 A | 7/1990 |
| JP | 7-24072 A | 1/1995 |
| JP | 8-141090 A | 6/1996 |
| JP | H08-141090 A | 6/1996 |
| JP | 10-43315 A | 2/1998 |
| JP | H10-43315 A | 2/1998 |
| JP | H11-506034 | 6/1999 |
| JP | 11-299901 A | 11/1999 |
| JP | H11-299901 | 11/1999 |
| JP | 2001-327609 A | 11/2001 |
| JP | 2002-521178 A | 7/2002 |
| JP | 2002-355316 A | 12/2002 |
| WO | WO 98/38947 | 9/1998 |
| WO | WO99/65419 | 12/1999 |
| WO | WO 00/04999 | 2/2000 |
| WO | WO 00/04999 A1 | 2/2000 |

* cited by examiner

|  | Pattern A | Pattern B | Pattern C |
|---|---|---|---|
| Diameter of Pore (um) | 30 | 50 | 100 |
| Interval between adjacent pores (um) | 250 | 125 | 250 |
| Density Pores (%) | 1.1 | 12.6 | 12.6 |

Portion of polymer film without coating which was positioned behind the stent skeleton before expansion of the stent and is exposed by the expansion Portions of polymer film with coating (portions with coating are deep in contrast because the portions are low in radiolucent property due to silver powder)

Fig.14a Fig.14b Fig.14c Fig.14d
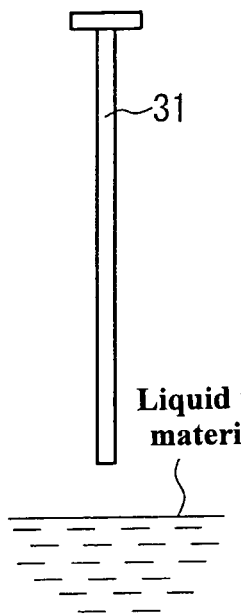
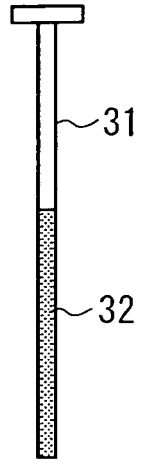
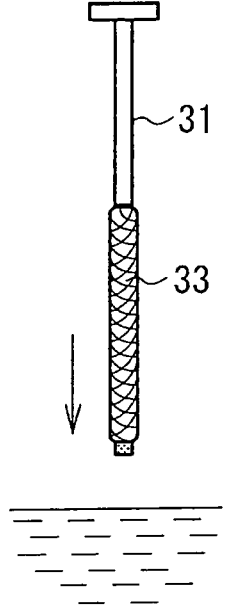
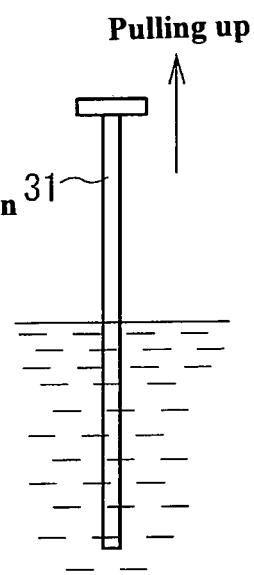
Fig.14e
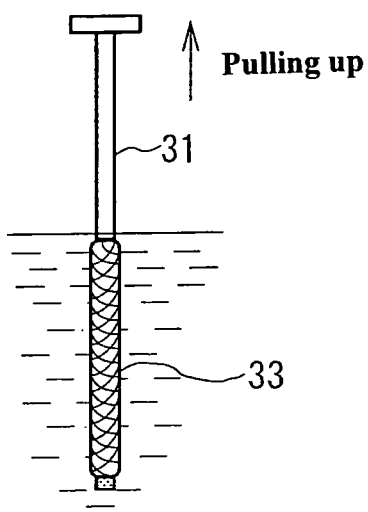
Fig.14f
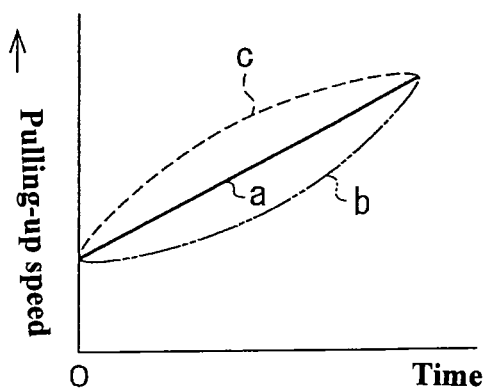

PROCESS FOR PRODUCING STENT

TECHNICAL FIELD

The present invention relates to a process for producing a stent (intraluminal graft) which is recently used for intravascular therapy and surgical operation, particularly to enlarge a coronary stenosis, a carotid stenosis, a biliary duct, or an esophagus or to block an aneurysm. More particularly, the present invention relates to a process for producing a stent comprising a plurality of tubular stent matrixes of which diameter is extendable and which are aligned at intervals in the longitudinal direction thereof and are covered and united by a polymer film.

BACKGROUND ART

Conventionally, ischemic heart diseases are generally treated by percutaneous transluminal cornary angioplasty (PTCA), that is, a procedure of introducing a balloon catheter to, for example, a narrowed part through a lumen of a blood vessel and, after that, inflating a balloon with liquid such as normal saline solution. However, this procedure has a problem of high possibility that an acute phase block of a coronary artery is caused and that the portion treated by PTCA is narrowed again (so-called post-PTCA restenosis). To solve the problem, intraluminal graft called stent has been developed. The stent recently rapidly came into practical use and are in widespread use. According to recent data, nearly 75% of procedures using balloon catheters have been already replaced by procedures using stents.

Stent matrix is an intraluminal graft which is implanted into a portion of a lumen to be treated through the lumen of a blood vessel or the like and is increased its diameter at the portion of the lumen to be treated so that the lumen is supported by action on the inside. Though the stent is mainly used in procedure for coronary artery so that the following description will be made mainly as to the procedure for coronary artery, the stent can be used for other lumens of human body such as biliary duct, esophagus, trachea, prostate, urinary duct, fallopian tube, aortic aneurysm, peripheral artery, renal artery, carotid artery, and cerebral blood vessel. As the application field of stent expands more and more, it is expected that stents will be used in many procedures including dilation of the narrowed portion, aneurysm embolization, cancer therapy, and the like, particularly that importance of microscopic stents will be increased according to the use in a field of cerebral surgery.

Through the spread of procedure using stent, restenosises have been dramatically prevented. On the other hand, however, since metallic stent matrixes are foreign substances in human body, a metallic stent matrix may thrombi a patient after several weeks from insertion of the metallic stent matrix. This is because the metallic stent itself is exposed to blood, resulting in adsorption of blood proteins such as fibrinogen and adherence or agglutination of blood platelets, thus forming thrombus. Further, thrombus may be formed because blood platelets are agglutinated on the convexes and concaves of a skeleton of the metallic stent matrix. Intimal thickening of a blood vessel due to cytokine discharged from blood platelets agglutinated on the periphery of the metallic stent matrix has been also pointed out as a problem. Accordingly, JP H11-299901A discloses to coat an outer periphery of a metallic stent matrix with a flexible polymer film having a number of fine pores.

FIG. 2 is a perspective view showing such a metallic stent matrix 10 having a mesh form to be used for a stent, FIG. 3 is a perspective view showing the stent matrix of FIG. 2 in the expanded state 10', and FIG. 4 is a perspective view showing a stent 20 comprising the stent matrix 10 of which outer periphery is coated with a flexible polymer film 19 having fine pores, and FIG. 5 is a perspective view showing the stent 20 in the expanded state, In biological tissues, inner walls of blood vessels and the like, that is, portions to be directly in contact with blood are coated with cell layer so-called endothelial cells. Since the surfaces of the endothelial cells are covered by sugar and the endothelial cells secrete substances that inhibit activation of blood platelets such as prostaglandin, thrombus is hardly formed in biological tissues. According to the stent disclosed in the aforementioned JP H11-299901A, the outer periphery of the metallic stent matrix is coated with a polymer film, thereby promoting proper endothelium formation with tissues and reducing thrombogenic property.

In JP H11-299901A, the polymer film for coating the outer periphery of the stent matrix is formed as follows. That is, a mandrel for a cover strip is first impregnated in a polymer solution, then is dried, and is perforated. After that, the mandrel is pulled out, thereby forming a membrane cover strip (envelope-shaped cover film). A stent matrix is inserted into the envelope-shaped cover film in a state that the cover film is sufficiently expanded by sending air into the cover film. After that, the sending of air is stopped so as to shrink the cover film, thereby forming a covering membrane on the outer periphery of the stent matrix.

OBJECTS OF THE INVENTION (1) According to the stent of JP H11-299901A, the outer periphery of the metallic stent matrix is covered by a flexible polymer film having fine pores so as to engraft endothelium on the surface of the film on the outer periphery of the stent matrix, thereby reducing the causing of thrombus formation. However, in the stent of JP H11-299901A, the inner periphery of the stent matrix is not covered with the polymer film so that the metallic stent matrix is exposed. There is still a problem of causing thrombus, allergic to metal, stimulus of tissues due to metal, and rust development. Since the inner periphery of the stent has convexes formed by stent struts composing the stent matrix, the convexes disarrange bloodstream, facilitating the formation of thrombi. The formed thrombi exfoliate and move downstream (travels peripherad through the bloodstream) so as to cause infarction in small blood vessel on the downstream side or platelet-derived growth factor discharged from blood platelets in the thrombi to stimulate to cause thickening. Therefore, the problem of causing intimal thrombus is serious at this portion.

The method of forming a polymer film as an outer covering membrane on the outer periphery of a stent matrix by inserting the stent matrix to an envelope-shaped cover film and shrinking the envelope-shaped cover film has the following problem. That is, as shown in FIGS. 2 and 3, the stent matrix 10 used in JP H11-299901A is formed of a cross-hatched lattice. When a polymer film as an outer covering membrane is formed on such a mesh stent matrix 10 by the aforementioned method, the outer covering membrane is bonded at contact points between the polymer film and the respective stent struts 11 composing the mesh stent matrix 10 as shown in FIG. 6. Accordingly, the integrity between the polymer film 19 and the stent matrix is poor.

Accordingly, when the stent matrix is expanded radially, the contact points between the stent struts 11 and the polymer film 19 slide and move. That is, the position of the polymer film 19 covering the outer periphery of the stent matrix is shifted when the stent is expanded.

In JP H11-299901A, the polymer film 19 has fine pores which are arranged to be spaced substantially equally. The purpose of the formation of fine pores is inhibiting formation of thrombi and intimal thickening by grafting endothelial cells on the inner wall of the stent. Therefore, it is believed that the pores are formed at positions other than the position directly above the stent skeleton. When the polymer film is shifted relative to the stent matrix during expansion of the stent, however, the fine pores may be occluded by the stent struts. If the fine pores are occluded, the arrangement design of the fine pores becomes worthless.

JP H11-299901A also describes that the polymer film is coated with biodegradable polymer or chemicals. When the inner periphery of the stent matrix is coated with such a functioning agent, the portions of the inner periphery of the polymer film where the struts of the mesh stent matrix are positioned are not coated with such a coating of the functioning agent. However, as the position of the polymer film is shifted relative to the stent matrix during the expansion of the stent, surfaces without coating of the functioning agent are exposed. The coating also becomes worthless.

In a paragraph [0040] of JP H11-299901A, it is described that the adhesion of the cover strip to the outer periphery of the stent matrix 10 may be secured by heat-sealing of sending heated air during the coating of the stent matrix with the cover strip. Though this operation increases the adhesion at contact points between the polymer film 19 and the stent struts 11 composing the mesh stent matrix, it is impossible to coat entire surfaces of the stent struts 11 by the polymer film 19. Since the stent matrix is generally formed by laser beam machining of a metallic tube, shape edges of stent struts formed by cutting are rounded by chemical polishing or sonic treatment so that the surface of the stent matrix is generally mirror finish. As well known, it is difficult to bond a resin material to a smooth surface of the metal. Similarly, it is not easy to bond the polymer film to the stent matrix. To cover the entire surfaces of the stent struts with the polymer film to increase the adhesion of the polymer film 19 relative to the struts, it is required to melt the cover strip for even a moment and press the cover strip against the stent matrix. For this, it is necessary to send significantly hot air. Since the cover strip is a thin film having fine pores, however, the polymer film may not maintain its shape because of the hot air capable of melting the polymer film, resulting in bursting, breakage, defects of pin holes, cracks, or the like.

It is an object of the first invention to overcome the problems of the stent of JP H11-299901A and to provide a stent in which a stent matrix is covered by a polymer layer with improved adhesion, thereby more securely preventing formation of thrombi and overcoming a problem of drift between the stent matrix and the covering layer.

It is each object of the second through fourth inventions to provide a process of producing a stent having reduced thrombus formation.

It is an object of the fifth invention to provide a stent having further reduced thrombus formation and excellent bendability.

Recently, as the application field of stent has expanded more and more, a stent matrix made of a flexible material having shape memory property allowing deformation of the stent into an arch has been developed in order to allow the stent to be inserted into a bent vascular channel and a stent matrix which is deformable into an arch during expansion has been developed because there is a need that the stent can be deformed while increasing its diameter according to the shape of a part (for example, a part bent into an arch) of a vascular channel where the stent will be implanted.

It is an object of the sixth invention to provide a stent which has further reduced thrombus formation, can be flexibly bent, and thus flexibly follow any deformation and expansion of stent matrixes.

It is an object of the seventh invention to provide a stent in which polymer films covering a stent matrix can flexibly follow the deformation and expansion of the stent matrix.

SUMMARY OF THE INVENTION (I) A stent of the first invention comprises a tubular stent matrix of which diameter is extendable and a flexible polymer layer coating said stent matrix, and is characterized in that the polymer layer is closely attached to and covers the entire surface of the stent matrix.

Since the flexible polymer layer is attached to and covers the entire surface of the stent matrix not only the outer periphery of the stent matrix, the stent has no problem of causing allergic to metal, stimulus of tissues due to metal, and rust development. Since the inner periphery of the stent is a flat and smooth surface covered by the polymer layer without convexes and concaves so as not to disarrange bloodstream, the formation of thrombus can be inhibited well. In addition, there is no problem of drift between the stent matrix and the polymer layer during the expansion of the stent, thereby maintaining the positional relationship between the stent matrix and the polymer layer before and after the expansion of the stent.

(II) A process of producing a stent of the second invention is a process of producing a stent comprising a tubular stent matrix of which diameter is extendable and flexible polymer films which are attached to both the inner periphery and the outer periphery of said stent matrix and have a plurality of fine pores formed therein, and is characterized by comprising: a step of forming a polymer film for outer layer by rotating a mold having a cylindrical inner bore about its axis and also supplying a liquid resin material into the mold; a step of supplying said stent matrix into the mold; a step of forming a polymer film for inner layer by rotating the mold about its axis and also supplying a liquid resin material into the mold; a step of releasing the stent matrix with the films from the mold.

Since the flexible polymer films cover not only the outer periphery but also the inner periphery of the stent matrix in the stent produced by the process of the second invention, the formation of thrombus can be inhibited well.

According to the process of the second invention, the respective polymer films for outer layer and for inner layer can be formed to have uniform thickness by centrifugal molding.

(III) A process of producing a stent of the third invention is a process of producing a stent having a tubular stent matrix of which diameter is extendable and flexible polymer films which are attached to both the inner periphery and the outer periphery of said stent matrix and have a plurality of fine pores formed therein, and is characterized by comprising: a step of forming the polymer film by impregnating a mandrel into a liquid resin material for forming the polymer film and pulling up the mandrel; and a step of equalizing the thickness of the polymer film by pulling up the mandrel in the vertical direction and controlling the pulling-up speed.

Since the flexible polymer films cover not only the outer periphery but also the inner periphery of the stent matrix in the stent produced by the process of the third invention, the formation of thrombus can be inhibited well.

According to the third invention, the thickness of the polymer film can be equalized all over the length in the longitudinal direction of the stent (that is, the direction of pulling up the mandrel) by controlling the pulling-up seed of the mandrel.

If the pulling-up speed is constant, the thickness of the film becomes larger the lower the position of the mandrel pulled up is, because of liquid resin material falling from the above. In the third invention, the thickness of the polymer film can be equalized all over the length in the longitudinal direction of the mandrel by gradually lowering the speed of pulling up the mandrel.

(IV) A process of producing a stent of the fourth invention is a process of producing a stent having a tubular stent matrix of which diameter is extendable and flexible polymer films which are attached to both the inner periphery and the outer periphery of said stent matrix and have a plurality of fine pores formed therein, and is characterized by comprising: a step of inserting a polymer film for inner layer into the stent matrix and overlaying a polymer film for outer layer onto the stent matrix; and a step of welding the respective polymer films to the stent matrix.

Since the flexible polymer films cover not only the outer periphery but also the inner periphery of the stent matrix in the stent produced by the process of the fourth invention, the formation of thrombus can be inhibited well.

According to the process of the fourth invention, the respective polymer films for outer layer and for inner layer can be easily formed to have uniform thickness by polymer films. It should be noted that the respective polymer films are securely bonded to the stent matrix by welding.

(V) A stent of the fifth invention comprises a plurality of stent matrixes of which diameter is extendable and polymer films which are attached to both the inner peripheries and the outer peripheries of said stent matrixes and have a plurality of fine pores formed therein, wherein the stent matrixes are aligned in the longitudinal direction thereof and are united by the polymer films.

Since the polymer films cover not only the outer peripheries but also the inner peripheries of the stent matrixes in the stent of the fifth invention, the formation of thrombus can be inhibited well. The stent of the fifth invention comprising a plurality of stent matrixes is excellent in bendability because the portions between adjacent stent matrixes can be flexibly bent.

(VI) A stent of the sixth invention comprises a plurality of stent matrixes which are aligned in the longitudinal direction thereof at intervals, a cylindrical outer polymer film which is overlaid on the outer peripheries of said stent matrixes, and a cylindrical inner polymer film which is laid on the inner peripheries of said stent matrixes, wherein said stent matrixes are united by the outer polymer film and the inner polymer film, and is characterized in that the outer polymer film and the inner polymer film allow the shift of the stent matrixes relative to the polymer films during expansion of the stent matrixes, and the outer polymer film and the inner polymer film are bonded to each other at portions between adjacent stent matrixes.

In the stent of the sixth invention, the shift of the stent matrixes relative to the outer polymer film and the inner polymer film during the expansion of the stent matrixes is allowed so that the stent matrixes expand while sliding between the outer polymer film and the inner polymer film. Therefore, the stent has no risk of twisting and/or tearing the polymer films. In addition, since the outer polymer film and the inner polymer film are bonded to each other at the portions between adjacent stent matrixes, the inner polymer film is drawn by the bonded portions during the expansion of the stent, the inner polymer film can follow the entire expansion. Therefore, even when the stent has a special configuration, both the outer periphery and the inner periphery of the stent can be covered by polymer films, thereby reducing the formation of thrombus with giving excellent bendability, deformation following property, and flexibility.

In the sixth invention, in order to allow shift of the stent matrixes relative to the outer polymer film and the inner polymer film, the outer polymer film and the inner polymer film are preferably not bonded to the stent matrixes. The outer polymer film and the inner polymer film may be partially bonded to the stent matrixes, preferably in the dot form.

(VII) A stent of the seventh invention comprises a stent matrix composed of a mesh tube of which diameter is extendable, a cylindrical outer polymer film overlaid on the outer periphery of said stent matrix, and a cylindrical inner polymer film laid on the inner periphery of said stent matrix, and is characterized in that the outer polymer film and the inner polymer film are not bonded to said stent matrix and are bonded to each other at least at some of meshes of said mesh stent matrix.

In the stent of the seventh invention, the outer polymer film and the inner polymer film covering the stent matrix are not bonded to the stent matrix so as to allow shift of the stent matrix relative to the outer polymer film and the inner polymer film so that the stent matrix expands while sliding between the outer polymer film and the inner polymer film. Therefore, the stent has no risk of twisting and/or tearing the polymer films. In addition, since the outer polymer film and the inner polymer film are bonded to each other at the meshes of the mesh stent matrix, the inner polymer film is drawn by the bonded portions during the expansion of the stent, the inner polymer film can follow the entire expansion. Therefore, even when the stent has a special configuration, both the outer periphery and the inner periphery of the stent can be covered by polymer films, thereby reducing the formation of thrombus with giving excellent bendability, deformation following property, and flexibility.

BRIEF DESCRIPTION OF THE DRAWINGS

FIGS. 14a-14f are explanatory illustrations of a process of the third invention;

FIG. 16b is an enlarged view of a portion B of FIG. 16a;

DETAILED DESCRIPTION

(I) Explanation of First Invention

Figure 2:
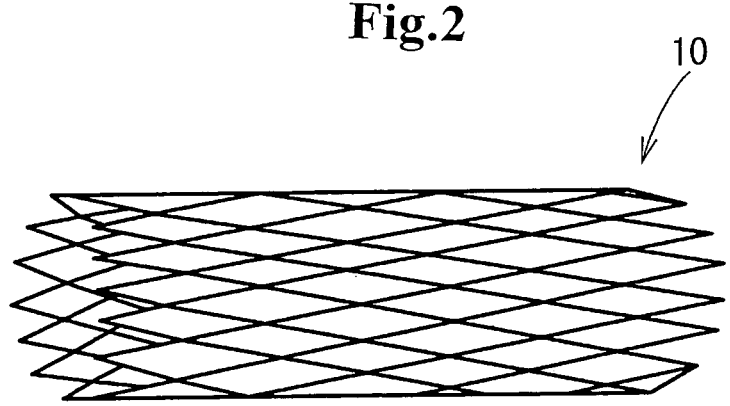
FIG. 2 is a perspective view of a stent matrix.

Preferably, a stent matrix composing a stent of the first invention is a tubular member having a length of from about 2 to 40 mm and a diameter of from about 1/10 to 1/2 of the length. The thickness of the stent matrix (wall thickness of the tubular member) is preferably from 11 to 2000 μm, more preferably from 51 to 500 μm, especially preferably from 101 to 300 μm. The stent matrix is preferably formed of a mesh so that the stent matrix can be flexibly expanded radially, particularly preferably, a cross-hatched lattice as shown in FIG. 2 in which the lattice extends in the helical direction.

The stent matrix is preferably made of a biocompatible metal. Examples of such a biocompatible metal include stainless steel, titanium, tantalum, aluminum, tungsten, nickel-titanium alloy, cobalt-chromium-nickel-iron alloy. When the stent matrix is made of nickel-titanium alloy, cobalt-chromium-nickel-iron alloy, or the like, the stent matrix is preferably subjected to heat treatment for shape memory. When the stent matrix is made of nitinol as one of nickel-titanium alloys, the heat treatment is conducted by converting the crystal structure of nitinol from martensite phase to austenite phase while the stent matrix is expanded, thereby memorizing the shape and giving self-expandability to the stent matrix. Other than metals, resins having excellent mechanical strength such as polyether ether ketone, aromatic polyamide, polyimide, and the like may be used for the base material of the stent.

Suitable material of the flexible polymer layer is a high-molecular elastomer having high flexibility. Examples of such a high-molecular elastomer include elastomer of polystyrene series, of polyolefin series, of polyester series, of polyamide series, of silicone series, of urethane series, of fluorocarbon resin series, and of natural rubber series, copolymers of these, and polymer alloys of these. Among these, a segmented polyurethane, a polymer of polyolefin series, and a polymer of silicone series are preferable, particularly, a segmented polyurethane having high flexibility and excellent mechanical strength is best.

The segmented polyurethane polymer has a flexible polyether section as its soft segment and a section containing highly aromatic rings and urethane bonds as its hard segment, wherein the soft segment and the hard segment are subjected to phase separation to form a fine structure. The segmented polyurethane polymer is excellent in antithrombogenicity and is also excellent in properties such as strength and ductility so that it can be sufficiently expanded without being broken when the stent is expanded radially.

The thickness ("d" in FIG. 1 as will be described later) of a polymer layer made of the segmented polyurethane polymer is preferably from 1 μm to 100 μm, particularly from 5 μm to 50 μm, especially from 20 μm to 50 μm.

The polymer layer is preferably provided with a plurality of fine pores. The fine pores may be arranged in random order. Preferably, the fine pores are formed to have substantially equal intervals therebetween. The phrase "substantially equal intervals" does not mean that the distances between fine pores are equal, but means that the fine pores are arranged at nearly regular intervals by a method of controlling the spaces between the fine pores. Accordingly, the arrangement with substantially equal intervals includes arrangements of oblique order, of circular order, of elliptic order, and the like which look random order at the first glance. The fine pores may have any size and any shape if the fine pore can allow passage of endothelial cells. The fine pores are preferably circular pores of which diameter is from 5 μm to 500 μm, preferably from 10 μm to 100 μm, more preferably from 20 μm to 100 μm. It should be understood that the fine pores may be pores of ellipse, square, rectangular, or other shape. This is true for the state before expansion. At a time when the stent is expanded and implanted in a lumen, the shape is varied from circle to ellipse and the diameter is also varied accordingly. The fine pores are aligned in a plurality of straight lines with intervals of from 51 μm to 10000 μm, preferably from 101 μm to 8000 μm, more preferably from 201 μm to 5000 μm. The plurality of straight lines are arranged in the axial direction of the stent with a predetermined constant angular interval from each other and are from 10 to 50 in number.

It should be noted that the best diameter and interval of the fine pores are in subservient relationship. The relationship can be easily understood by assuming the relationship as the density of pores in the polymer layer. That is, when substantially circular pores are arranged at nearly equal intervals just like three patterns shown in FIG. 7, the density per unit area naturally depends on the diameter and the interval of the fine pores.

Figures 7, 8:
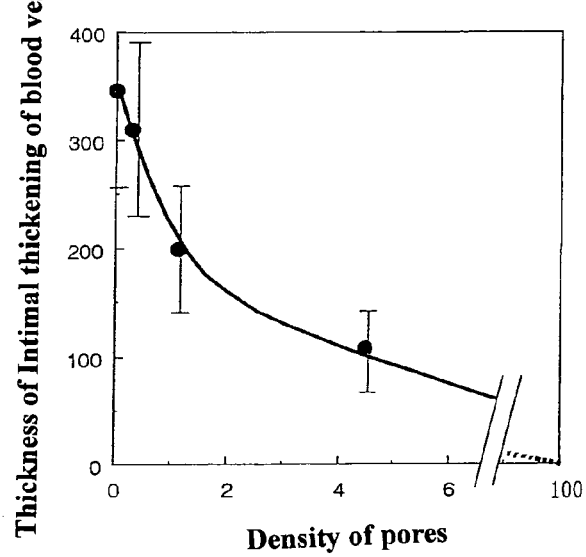
FIG. 7 is an explanatory illustration showing relations of pattern of fine pores of a polymer layer relative to diameter, interval, and density of the fine pores.
FIG. 8 is a graph showing a relation between density of pores of the polymer layer and the thickness of the intimal thickening of a blood vessel caused by implantation of a stent into the blood vessel.

The relation between the density of pores and the thickness of the intimal thickening of a blood vessel caused by implantation of the stent into the blood vessel is shown in FIG. 8.

From FIG. 8, it is found that the preferable diameter and interval of fine pores are in relationship with the density of pores. It should be understood that, even with preferable density of pores, too small diameter of pores is not preferable because the growth of endothelial cells on the inner side of the stent must be poor and, on the other hand, too large diameter of pores is also not preferable because the strength of the polymer layer must be poor and ingression of endothelial tissues must be excessive.

The polymer layer may be coated with a biodegradable polymer (bioabsorbable polymer). Examples of such a biodegradable polymer include gelatine, poly-lactic acid, polyglycolic acid, caprolactone, lactic-glycol acid copolymer, polygioxisanone, and chitin.

The biodegradable polymer may contain a therapeutic drug such as an antiplatelet drug, an antithrombotic drug, a growth accelerator, a growth inhibitor, and an immune-suppressing drug. The therapeutic drug is discharged into living body according to the degradation of the biodegradable polymer and thus provide effects of inhibiting formation of thrombus, inhibiting growth of smooth muscle cells so as to prevent constriction, inhibiting growth of cancerous cells, or promoting the growth of endothelial cells so as to achieve early formation of endothelium lining.

Examples of such a therapeutic drug include heparin, low-molecular heparin, hirudin, argatroban, formacolin, vapiprost, prostamoline, prostakilin homolog, dextran, D-phe-pro-arg chloromethyl ketone, dipyridamole, platelet receptor antagonist of glycoprotein, recombinant hirudin, thrombin inhibitor, vascular heptyne, angiotensin-converting enzyme inhibitor, steroid, fibrocyte growth factor antagonist, fish oil, omega 3 fatty acid, histamine, antagonist, HMG-CoA reductase inhibitor, seramin, serotonin blocker, thioprotease inhibitor, triazolopyrimidine, interferon, vascular endothelial growth factor (VEGF), rapamycin, and FK506. Further, such a therapeutic drug may be a statin drug having a function of melting plaque such as mevalotin, fuluvastatin, or the like.

The polymer layer on the outer peripheral side of the stent may be coated with a lubricative substance in order to smooth the movement of the stent within a fine blood vessel in a human body. Examples of such a lubricative substance include low-molecular hydrophilic substances such as glycerin, biocompatible substances such as hyaluronic acid and gelatine, and synthetic hydrophilic polymers such as polyethylene glycol, polyacrylamide, polydimethyl acrylamide, and polyvinylpyrrolidone.

The stent of the first invention in which the entire surface of the stent matrix is coated with the polymer layer wherein the polymer layer is closely attached to the entire surface of the stent matrix can be produced by either of the following processes (1) and (2). The process of producing the stent matrix of the first invention is not limited to these processes (1) and (2).

(1) A process comprising: according to the process of the second invention as will be described later, rotating a mold having a cylindrical inner bore about its axis and also supplying a polymer solution into the mold so as to form an outer polymer layer, inserting a stent matrix into the mold, then rotating the mold about its axis and also supplying a polymer solution into the mold so as to form an inner polymer layer, and after that, releasing the stent matrix with layers from the mold.

In this process, preferably a cylindrical mold having a cylindrical inner periphery is used. While rotating the mold about its axis, a polymer solution for an outer polymer layer is supplied into the mold so that an outer polymer layer is formed by centrifugal action.

The polymer solution may be a solution of polymer or a polymerized solution of monomer. As the polymer solution, a segmented polyurethane polymer solution prepared from an organic solvent such as dioxane or tetrahydrofuran may be used. As the polymerized solution of monomer, a deacetonated, dealcoholized, or deoximated silicon rubber of condensation hardening type may be used.

There is no preference in whether the supply of the polymer solution or the rotation of the mold is started in fist. However, it is preferable to supply the polymer solution into the mold while rotating. It is preferable to move the position for injecting the polymer solution along the axial direction of the mold so as to supply the polymer solution to a wide area in the mold uniformly.

After a coating of the polymer solution for outer layer on the inner surface of the mold, the stent matrix is inserted into the mold. Then, a polymer solution for forming the inner layer is supplied to the inside of the mold and the inner polymer layer is formed by centrifugal action. After the inner polymer layer is subjected to hardening treatment such as drying, ultraviolet irradiation, or heating treatment, the stent intermediate is released from the mold. The stent intermediate is perforated.

It is preferable to supply the stent matrix into the mold after the coating of the polymer solution for outer layer is formed along the inner surface of the mold and is then subjected to hardening treatment such as drying or ultraviolet irradiation. The stent matrix may be supplied into the mold directly or after being subjected to prewetting by impregnating the stent matrix into liquid resin material.

A coating of the aforementioned biodegradable polymer on the outer polymer layer may be formed by supplying a polymer solution for the biodegradable polymer into the mold to form a first layer and, after that, supplying a polymer solution of the aforementioned segmented polyurethane polymer or the like into the mold so as to form a second layer by centrifugal action. Similarly, a coating of the biodegradable polymer on the inner polymer layer may be formed by supplying a polymer solution of the aforementioned segmented polyurethane polymer or the like into the mold to form a first layer by centrifugal action and, after that, supplying a polymer solution of the biodegradable polymer into the mold to form a second layer.

A coating of the biodegradable polymer may be formed by first obtaining a stent intermediate in the aforementioned manner using a polymer solution for the segmented polyurethane polymer or the like and, after releasing the stent intermediate from the mold, impregnating the stent intermediate into a polymer solution of the biodegradable polymer. In this case, the coating may be formed by promoting polymerization using ultraviolet lays or the like after taking out the stent intermediate from the biodegradable polymer solution.

By adding a therapeutic drug into the biodegradable polymer solution, a coating containing the therapeutic drug is formed. By adjusting the kind and the molecular weight of the biodegradable polymer and the thickness of the coating, the time and period when the therapeutic drug is discharged into the body can be controlled.

As mentioned above, the fine pores are formed in the stent intermediate by laser or the like after the mold removal. There is no preference in whether the formation of the coating of a biodegradable polymer or a lubricative polymer or the formation of fine pores by laser machining is performed in first. However, the description has been made here with a method of performing the formation of fine pores by laser machining after the coating formation.

(2) A process comprising: according to the process of the third invention as will be described later, impregnating a mandrel in a polymer solution, pulling up the mandrel in the vertical direction so as to form an inner polymer layer, attaching a stent matrix to the mandrel having the inner polymer layer so that the stent matrix is overlaid onto the mandrel, then impregnating the mandrel with the stent matrix into the polymer solution, pulling up the mandrel with the stent matrix so as to form an outer polymer layer, and then pulling out the mandrel.

That is, a mandrel is impregnated into a polymer solution slowly not to entrap air bubbles, is then pulled up in the vertical direction, and is subjected to hardening treatment such as drying or ultraviolet irradiation, if necessary, so as to form an inner polymer layer. In case of using a solution of polymer as the polymer solution, the drying is suitable as the hardening treatment. In case of using a polymerized solution of monomer as the polymer solution, the ultraviolet irradiation or heat hardening is suitable as the hardening treatment.

Then, the stent matrix is attached to the mandrel having the inner polymer layer thus formed such that the stent matrix is overlaid onto the mandrel. The mandrel with the stent matrix attached is impregnated into the polymer solution slowly and is then pulled up in the vertical direction so as to form an outer polymer layer. After the outer polymer layer is subjected to hardening treatment, the mandrel is pulled out, thereby producing a stent intermediate. Since the inner polymer layer and the outer polymer layer of the stent intermediate thus produced generally protrude from the both ends of the stent matrix, the excess protruding portions of the polymer layers are cut off.

For forming a biodegradable polymer layer, the mandrel is impregnated into the biodegradable polymer solution, i.e. the mandrel is subjected to the same coating treatment as mentioned above before the formation of the inner polymer layer or after the formation of the outer polymer layer. By adding a therapeutic drug into the biodegradable polymer solution, a coating containing the therapeutic drug is formed. By adjusting the kind and the molecular weight of the biodegradable polymer and the thickness of the coating, the time and the period when the therapeutic drug is discharged into the body can be controlled. The same is true for the formation of a lubricative polymer layer.

The fine pores can be formed by laser machining to penetrate the inner polymer layer and the outer polymer layer before or after pulling out the mandrel.

For pulling out the mandrel from the stent intermediate thus obtained, the mandrel is impregnated into an organic solvent which allows the polymer film to slightly swell preferably at a cubical expansion of 10% or less, thereby easily pulling out the mandrel from the stent intermediate. The kind of the organic solvent and the impregnating time depend on the material of the polymer film. For example, in case of using a segmented polyurethane resin for the polymer film, the mandrel is preferably impregnated into lower alcohol, preferably methanol or ethanol, particularly into methanol preferably for 1-30 hours, particularly for 5-20 hours. This facilitates the drawing of the mandrel. The reasons are considered, though remaining incompletely understood, that the polymer film slightly swells so that the adhesion between the polymer film and the mandrel is reduced and that the lower alcohol has affinities both to the metal and the polymer layer and low surface tension so that the lower alcohol enters into a boundary face between the metallic mandrel and the inner polymer layer so as to reduce adherence between the surface of the mandrel and the polymer layer and improve the sliding property.

Figure 1:
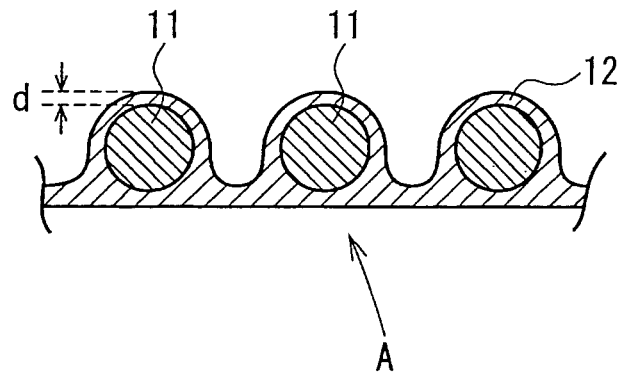
FIG. 1 is a schematic sectional view of a stent of the first invention, showing a state coated with a polymer layer.

In the stent of the first invention produced in the aforementioned manner, as shown in FIG. 1 as its sectional view, a polymer layer 12 closely adheres and coats the entire surfaces of stent struts 11 composing a mesh stent matrix. The inner surface A of the stent is a flat and smooth surface of the polymer layer 12. Since this stent has absolutely no exposed surface of the metallic stent matrix, the problem of causing allergic to metal, stimulus of tissues due to metal, and rust development is solved. The problem of formation of thrombus is also solved. Particularly, the inner surface is a flat and smooth surface without convexes and concaves, thereby solving the formation of thrombus on convexes and concaves. In addition, there is no problem of displacement between the polymer layer and the stent matrix before and after the expansion of the stent.

The coating thickness of the polymer layer represents the thickness of a part of the polymer layer 12 directly coating the stent strut 11, designated by "d" in FIG. 1.

Example 1

As the stent matrix, a mesh stent matrix 10 having a diameter of 4 mm, a length of 20 mm, and a thickness of 0.2 mm shown in FIG. 2 was employed.

Figure 3:
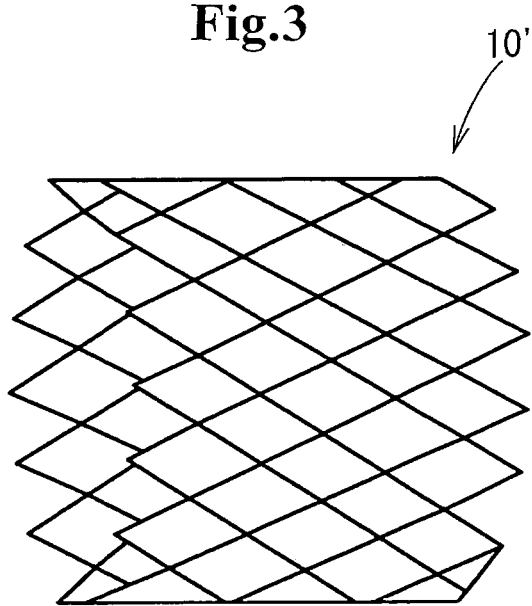
FIG. 3 is a perspective view of the stent matrix in a state that its diameter is increased.

FIG. 3 is a perspective view of the metallic stent matrix 10' after being expanded. The metallic stent matrix 10' in this state has a diameter of 8 mm, a length of 20 mm, and a thickness of 0.2 mm.

A stent was produced by coating the entire surfaces of the metallic stent matrix 10 with a segmented polyurethane polymer layer. As described concretely, a mandrel made of SUS316 was impregnated into a polyurethane solution to form a polyurethane layer for coating a cylindrical outer surface of the mandrel. The metallic stent matrix which was slightly expanded was overlaid on the polyurethane layer with significant pressure. The mandrel with the stent matrix was impregnated into the polyurethane solution to form a coating so that both the inner and outer peripheries of the stent matrix were coated. After laser machining, the portions of the films protruding from the both ends were cut out. The mandrel with the stent intermediate was impregnated into ethanol and the stent intermediate was pulled out from the mandrel.

The polyurethane solution was prepared by dissolving 10% by weight of Capdiomat (trade name) SPU: segmented polyurethane (available from Kontoron Cardiovascular Inc.) into a mixed solution of tetrahydrofuran and dioxane.

The polyurethane polymer layer thus formed was perforated by excimer laser to have pores having a diameter of 100 µm such that the pores were substantially equally arranged at intervals of 200 µm. Pores aligned along 24 lines in total were formed by repeating a process of turning the stent intermediate at 15° in the circumferential direction after forming pores in a line in the longitudinal direction.

Figure 4:
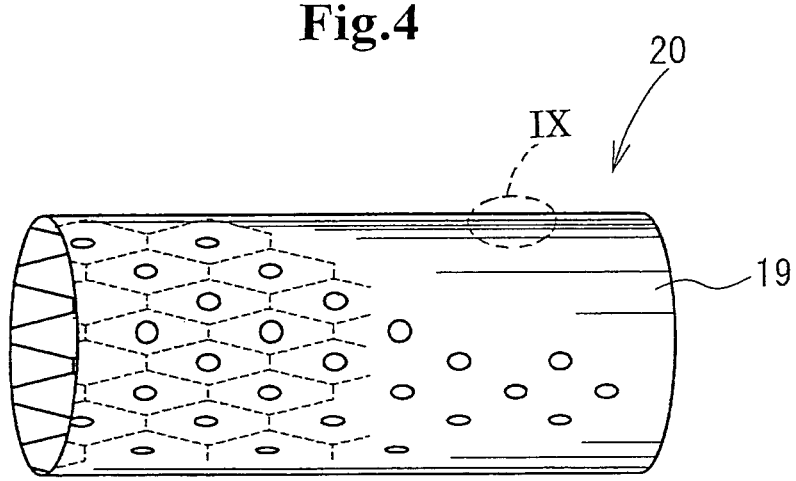
FIG. 4 is a perspective view of a stent.
Figure 5:
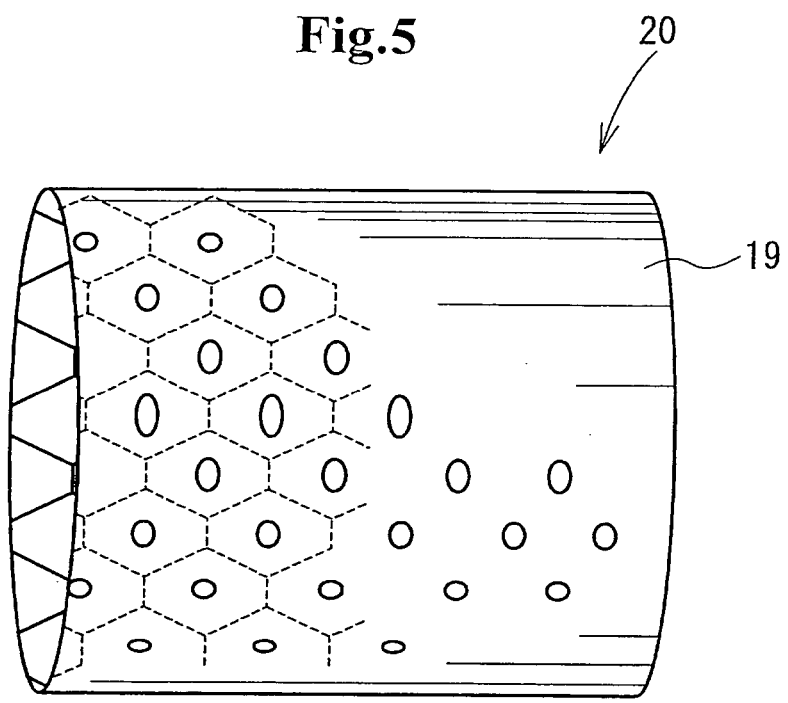
FIG. 5 is a perspective view of the stent in a state that its diameter is increased.
Figure 9:
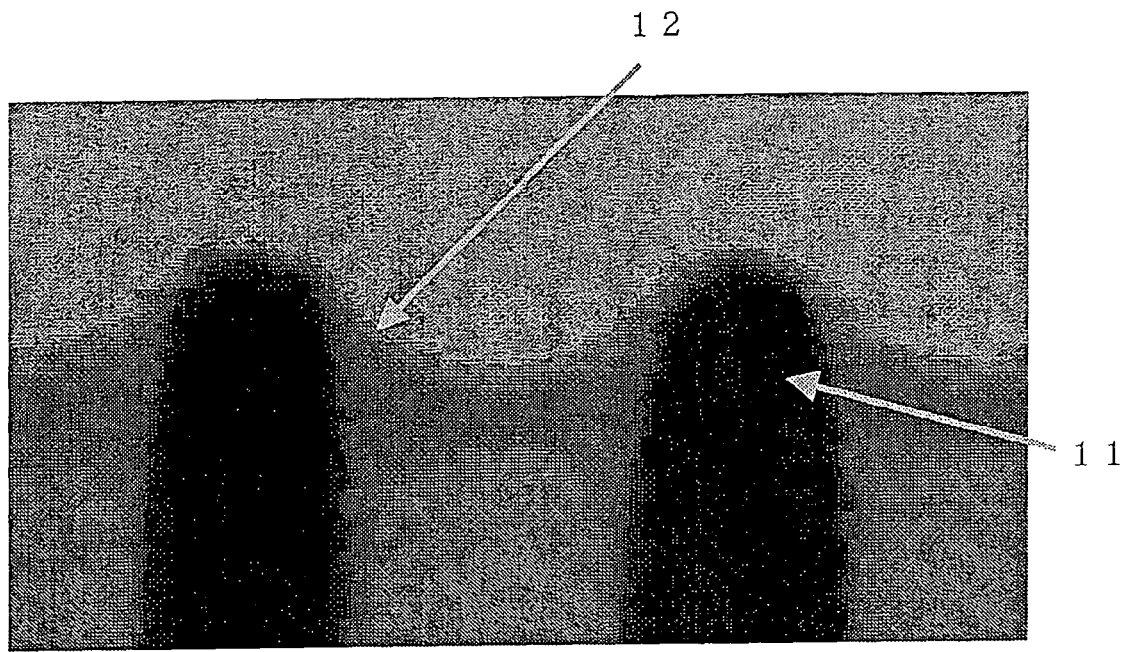
FIG. 9 is an X-ray transmission image of a stent of Example 1.

An X-ray transmission image of the stent thus obtained was taken by an X-ray microscope system (Model 1072, available from Skyscan). The X-ray transmission image is FIG. 9. The coating thickness "d" was 25 µm. FIG. 9 corresponds to a portion IX of the stent shown in FIG. 4, but shown as an enlarged image.

As shown in FIG. 1, in the stent, the entire surfaces of lattice-like struts 11 of the stent matrix are coated with the polyurethane polymer layer 12 with well adhesion. It is found that, even when the stent skeleton is moved according to the expansion of the stent matrix, the polyurethane polymer layer follows this movement, thus maintaining the positional relationship between the polymer layer and the stent. It is also found that the projecting structure of the stent struts as a factor of blocking bloodstream is laminated by the polymer film so as to have a flat and smooth surface.

Comparative Example 1

Figure 6:
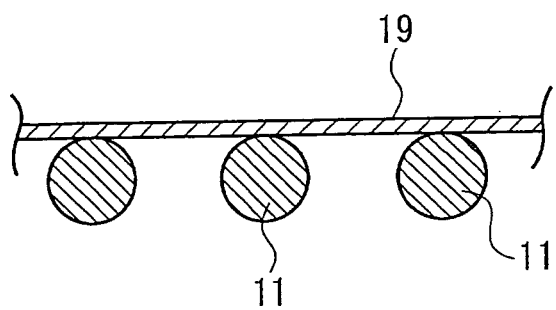
FIG. 6 is a schematic sectional view of a stent of JP H11-299901A, showing a state coated with a polymer film.
Figure 10:
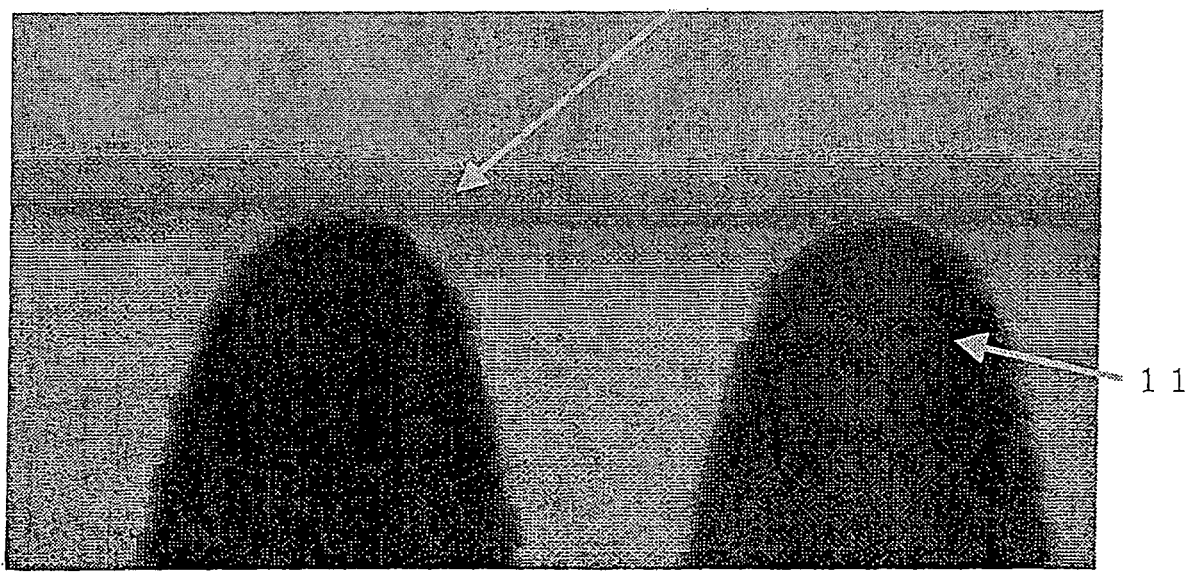
FIG. 10 is an X-ray transmission image of a stent of Comparative Example 1.

A coating of a polyurethane polymer film was formed only on the outer periphery of a stent matrix by the method described in JP H11-299901A. Fine pores were formed in the same manner as Example 1. An X-ray transmission image of the stent thus obtained was taken by the same way as Example 1. The X-ray transmission image is FIG. 10. It is found that, in the stent, the polymer film covers and is in contact with the outer periphery of the stent matrix by points (lines) as shown in FIG. 6, that is, the polymer film is fixed only by contact points. It is pointed out that the contact points are shifted by slide movement during the expansion of the stent.

These stents were grafted in carotid arteries of a rabbit. Observation was conducted after one month. The results are shown in Table 1, FIGS. 11a, 11b and FIG. 12.

Figure 11A:
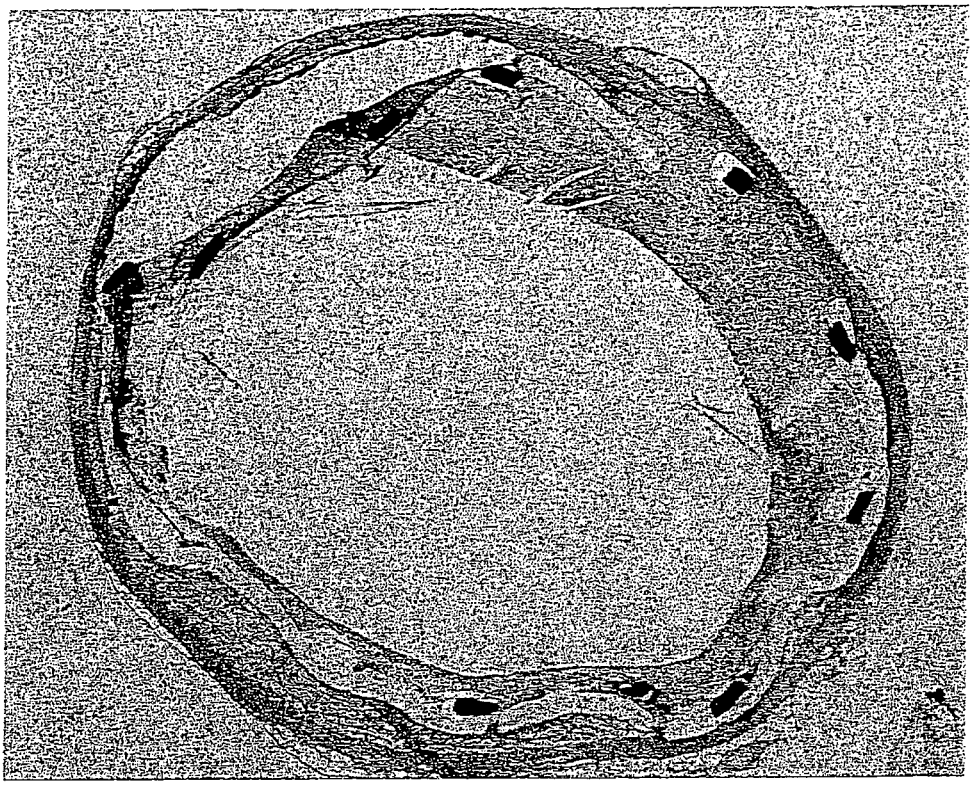
FIG. 11a is a photomicrograph of the stent after one month from implantation in Comparative Example 1 and FIG. 11b is a photomicrograph of the stent after one month from implantation in Example 1.
Figure 11B:
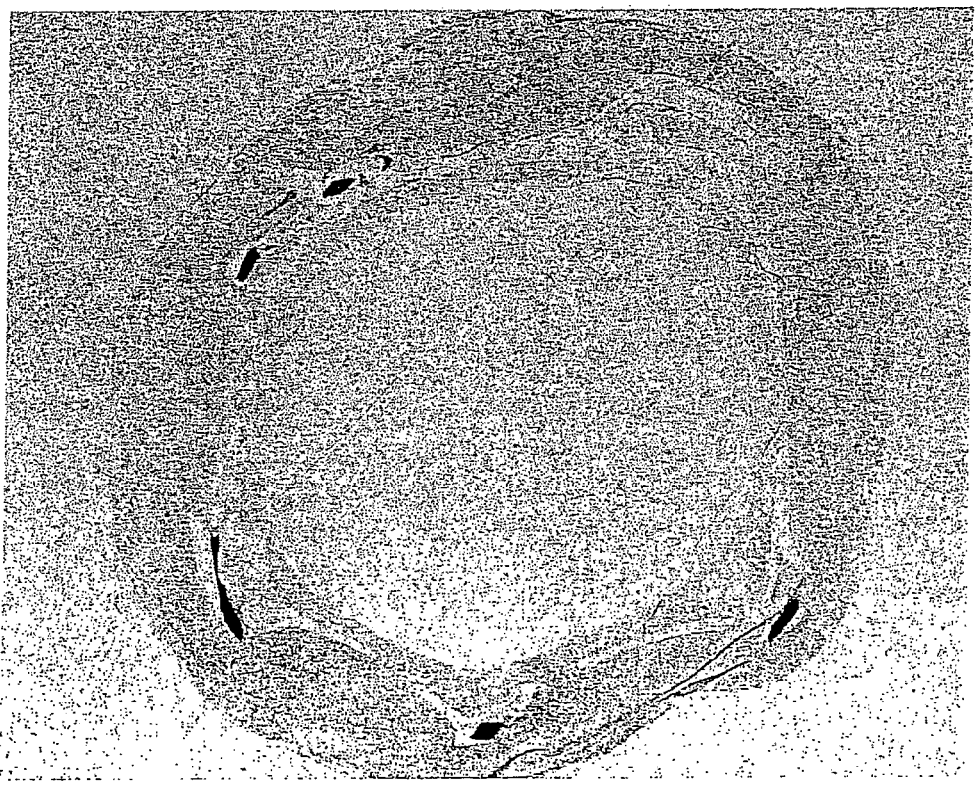
Figure 12:
FIG. 12 is a photomicrograph of a section of biological tissue where the stent is implanted in Comparative Example 1.

FIG. 11a shows Comparative Example 1 and FIG. 11b shows Example 1. Positioned outside the polymer layer is an existing intima and positioned inside the polymer layer is a neogenetic intima. As apparent from FIGS. 11a, 11b, the thickness of the intimal thickening of Example 1 (FIG. 11b) is thinner than that of Comparative Example (FIG. 11a). As shown in FIG. 12, since the stent struts project into blood stream in Comparative Example 1, thrombus may be easily formed around the struts so that platelet-derived growth factors and the like are discharged, resulting in intimal thickening. On the other hand, since the surface facing the bloodstream was a flat and smooth surface of the polymer layer in Example 1, the formation of thrombus was prevented.

TABLE 1

Comparison of intimal thickening

|  | Thickness of intimal thickening (μm) | Area ratio between neogenetic intima and existing intima (%) |
|---|---|---|
| Comparative Example 1 | 304.6 (n = 7) | 302.9 |
| Example 1 | 239.9 (n = 7) | 266.7 |

Comparative Example 2

Figure 13:
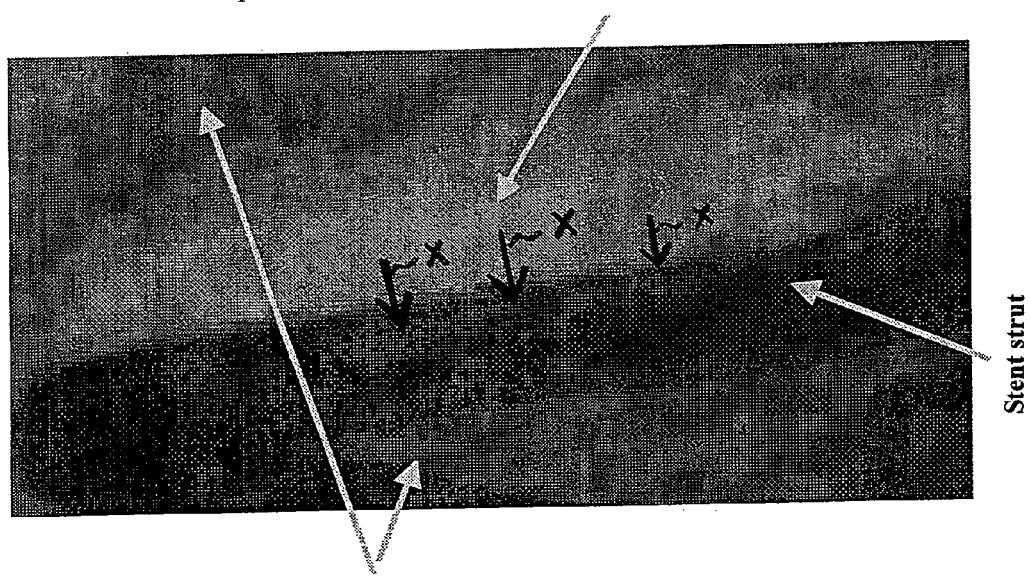
FIG. 13 is an X-ray transmission image of the stent which is expanded after coating the inner wall of the stent in Comparative Example 2.

A mixed aqueous solution containing 5% of photoreactable gelatine of spiron benzophenone series, 2.5% of heparin, and 0.1% of silver powder was prepared. The stent produced in Comparative Example 1 was placed horizontally statically and the mixed solution was dropped to the inner wall of the stent at an amount of 20 μL per 1 $cm^2$. The dropped solution was stretched uniformly by a round bar made of PTFE and was exposed to light to fix a coating. This procedure was repeated twice. The stent of which inner wall was thus coated was expanded in air by a balloon catheter and, after that, was observed by an X-ray microscope. An X-ray transmission image taken of this stent is FIG. 13.

From the above, it is found that portions where the stent struts existed before expansion were coated with no agent and sliding phenomenon between the stent struts and the polymer film was caused by the expansion so that the portions coated with no agent were exposed outside. The fine pores formed in Comparative Example 1 moved or slid on the polymer layer so that the fine pores were positioned behind the radiopaque stent struts as shown by arrows X. As a result, the fine pores were not observed in the X-ray transmission image of FIG. 13. This means that the fine pores were blocked. Therefore, it is pointed out that, since the diameter and intervals of pores which are strictly designed are varied by the expansion of the stent matrix as shown in FIG. 8, the density of pores is also varied, thus bringing about a problem of intimal thickening.

According to the stent of the first invention, since the polymer layer is closely attached to the entire surface of the stent matrix, excellent biocompatibility can be given to the stent, thereby preventing adverse effects to human tissues such as allergy and thrombus due to metal. In addition, the stent has no problem of displacement between the stent matrix and the polymer layer during the expansion of the stent.

(II) Explanation of Second Invention

The dimension, configuration, and material of a stent matrix employed in a process of producing a stent of the second invention are the same as those of the suitable stent matrix of the first invention.

As for the material and thickness of a flexible polymer film, fine pores, biodegradable polymers to be coated on the outer periphery of an outer polymer film and on the inner periphery of an inner polymer film, methods of forming these coatings, therapeutic drugs to be contained in the biodegradable polymers, and a lubricative substance to be coated on the outer surface of the outer polymer film, the same description about the flexible polymer layer in the first invention can be adopted to this invention.

In a process of producing a stent of the second invention, an outer polymer film and an inner polymer film both are formed by centrifugal molding method.

That is, preferably a cylindrical mold having a cylindrical inner periphery is used. While rotating the mold about its axis, a liquid resin material for an outer polymer film is supplied into the mold so that an outer polymer film is formed by centrifugal action.

The polymer solution may be a solution of polymer or a polymerized resin solution such as monomer.

There is no preference in whether the supply of the liquid resin material or the rotation of the mold is started in fist. However, it is preferable to supply the liquid resin material into the mold while rotating. It is preferable to move the position for injecting the liquid resin material along the axial direction of the mold so as to supply the liquid resin material to a wide area in the mold uniformly.

After a coating of the liquid resin material for outer layer on the inner surface of the mold, the stent matrix is inserted into the mold. Then, a liquid resin material for forming the inner polymer film is supplied to the inside of the mold and the inner polymer film is formed by centrifugal action. After the inner polymer film is subjected to hardening treatment such as drying, ultraviolet irradiation, or heating treatment, the stent intermediate is released from the mold. The stent intermediate is perforated.

It is preferable to supply the stent matrix into the mold after the coating of the liquid resin material for outer layer is formed along the inner surface of the mold and is then subjected to hardening treatment such as drying or ultraviolet irradiation. The stent matrix may be supplied into the mold directly or after being subjected to prewetting by impregnating the stent matrix into liquid resin material.

A coating of the aforementioned biodegradable polymer on the outer polymer film may be formed by supplying the biodegradable polymer solution into the mold to form a first layer and, after that, supplying a liquid resin material of elastomer such as the aforementioned segmented polyurethane polymer into the mold so as to form a second layer by centrifugal action. Similarly, a coating of the biodegradable polymer on the inner polymer layer may be formed by supplying a liquid resin material such as the aforementioned segmented polyurethane polymer into the mold to form a first layer by centrifugal action and, after that, supplying a liquid resin material of the biodegradable polymer into the mold to form a second layer.

A coating of the biodegradable polymer may be formed by first obtaining a stent intermediate using a liquid base resin material such as the segmented polyurethane polymer and, after releasing the stent intermediate from the mold, impregnating the stent intermediate into a liquid resin material of the biodegradable polymer.

Fine pores are formed in the stent intermediate released from the mold in the same manner as mentioned above.

In case of containing a therapeutic drug into the biodegradable polymer of the coating of the biodegradable polymer, it is preferable to add the therapeutic drug to the biodegradable polymer solution. By adjusting the kind and the molecular weight of the biodegradable polymer and the thickness of the coating, the time and the period when the therapeutic drug is discharged into the body can be controlled.

In case of forming a coating layer of a biodegradable polymer or a lubricative polymer, fine pores are formed by laser machining after the formation of the coating layer.

In the second invention, a single stent may be composed of two or more stent matrixes which are arranged coaxially and slightly spaced apart from each other. In such a stent, a portion between the stent matrixes can be flexibly bent.

Example 2

As the stent matrix, a mesh stent matrix 10 having a diameter of 3.2 mm, a length of 20 mm, and a thickness of 0.2 mm shown in FIG. 2 was employed.

FIG. 3 is a perspective view of the metallic stent matrix 10' after being expanded. The metallic stent matrix 10' in this state has a diameter of 8 mm, a length of 20 mm, and a thickness of 0.2 mm.

A stent was produced by coating the inner periphery and the outer periphery of the metallic stent matrix 10 with segmented polyurethane polymer films 19. As described concretely, a mold having an inner diameter of 3.5 mm was rotated at 6000 rpm and a polyurethane solution was supplied into the mold while moving the injection position along the axial direction of the mold, and heating the polyurethane solution in the mold at 60° C., thereby forming a polymer film as an outer layer having a thickness of 50 μm. After the stent matrix was inserted into the mold, a polyurethane solution was supplied to form a film while rotating the mold in the same manner, thereby forming a stent intermediate of which both surfaces were coated. The thickness of the polymer film for inner layer was 30 μm. The stent intermediate was processed by laser machining after being released from the mold, thereby producing a stent.

The polyurethane solution was prepared by dissolving 10% by weight of segmented polyurethane, a trade name Capdiomat, (available from Kontoron Cardiovascular Inc.) into a mixed solution of tetrahydrofuran and dioxane.

As the laser machining, excimer laser was employed to form pores having a diameter of 100 μm such that the pores were substantially equally arranged at intervals of 200 μm. Pores aligned along 24 lines in total were formed by repeating a process of turning the stent intermediate at 15° in the circumferential direction after forming pores in a line in the longitudinal direction.

The stent was grafted in a carotid artery of a rabbit. Observation was conducted after one month. As a result, it was observed that the intimal thickening was thin and the formation of thrombus was prevented.

The metal stent produced according to the process of the second invention can prevent adverse effects to human tissues such as thrombus due to metal. Particularly, since the polymer films are attached to the inner periphery and the outer periphery of the stent matrix, excellent biocompatibility can be given to the stent.

(III) Explanation of Third Invention

The dimension, configuration, and material of a stent matrix employed in a process of producing a stent of the third invention are the same as those of the suitable stent matrix of the first invention.

As for the material and thickness of a flexible polymer film, fine pores, biodegradable polymers to be coated on the outer periphery of an outer polymer film and on the inner periphery of an inner polymer film, methods of forming these coatings, therapeutic drugs to be contained in the biodegradable polymers, and a lubricative substance to be coated on the outer surface of the outer polymer film, the same description about the flexible polymer layer in the first invention can be adopted to this invention.

In the process of producing a stent of the third invention, as shown in FIGS. 14a, 14b, a mandrel 31 is impregnated into a liquid resin material slowly not to entrap air bubbles, is then pulled up in the vertical direction, and is subjected to hardening treatment such as drying or ultraviolet irradiation, if necessary, so as to form an inner polymer film 32 as shown in FIG. 14c.

In case of using a solution of polymer as the liquid resin material, the drying is suitable as the hardening treatment. In case of using a monomer solution as the liquid resin material, the ultraviolet irradiation or heat hardening is suitable as the hardening treatment.

In this invention, the distribution of thickness of the inner polymer film 32 is made uniformly in the longitudinal direction of the mandrel 31 by gradually lowering the pulling-up speed of pulling up the mandrel. The pulling-up speed may be lowered in a linear fashion as indicated by a solid line "a" in FIG. 14f and may be lowered with decelerating speed as indicated by a double-dashed line "b". Alternatively, the pulling-up speed may be lowered such that degree of the decelerating speed may be gradually reduced as shown by dashed line C. Normally, it is preferable to take a deceleration pattern indicated by the solid line "a" or the double-dashed line "b". The deceleration is preferably continuously conducted. This does not mean exclusion of stepwise deceleration.

Then, as shown in FIG. 14d, a stent matrix 33 is attached to the mandrel 31 having the inner polymer layer thus formed such that the stent matrix 33 is overlaid onto the mandrel 31. As shown in FIG. 14e, the stent matrix 33 is impregnated into the liquid resin material slowly and is pulled up in the vertical direction so as to form an outer polymer film. The pulling-up speed of this time is also controlled to have a pattern being gradually lowered in the same manner as the case of the inner polymer film 32.

After the outer polymer film is subjected to hardening treatment, the mandrel 31 is pulled out, thereby producing a stent. Since the inner polymer film and the outer polymer film of the stent thus produced generally protrude from the both ends of the stent matrix 33, the excess protruding portions of the polymer films are cut off.

As mentioned above, the liquid resin material for forming the polymer films may be polymer solution or solution of a monomer. The polymer solution is preferable because polymerization is not required so that the formation of film is easy.

Just like the second invention, also in the third invention, a therapeutic drug may be contained into the biodegradable polymer solution. By applying this biodegradable polymer, a coating layer of the biodegradable polymer containing the therapeutic drug can be formed. By adjusting the kind and the molecular weight of the biodegradable polymer and the thickness of the coating, the time and the period when the therapeutic drug is discharged into the body can be controlled.

After the outer polymer film is hardened, fine pores are formed to penetrate the inner polymer film 32 and the outer polymer film before or after pulling out the mandrel 31. The fine pores are preferably formed by laser machining.

In the third invention, for pulling out the mandrel from the stent thus obtained, the mandrel is impregnated into an organic solvent which allows the polymer film to slightly swell preferably at a cubical expansion of 10% or less, in the same manner as described in the first invention, thereby easily pulling out the mandrel from the stent. The kind of the organic solvent and the impregnating time depend on the material of the polymer film. For example, in case of using a segmented polyurethane resin for the polymer film, the mandrel is preferably impregnated into lower alcohol, preferably methanol or ethanol, particularly into methanol preferably for 1-30 hours, particularly for 5-20 hours. This facilitates the drawing of the mandrel.

Though only a single stent matrix 33 is overlaid onto the mandrel 31 as shown in FIG. 14d in the aforementioned embodiment, two or more stent matrixes may be overlaid onto the mandrel with being slightly spaced apart from each other. In such a stent, a portion between the stent matrixes can be flexibly bent.

Example 4

As the stent matrix, a mesh stent matrix 10 having a diameter of 4 mm, a length of 20 mm, and a thickness of 0.2 mm shown in FIG. 2 was employed.

FIG. 3 is a perspective view of the metallic stent matrix 10' after being expanded. The metallic stent matrix 10' in this state has a diameter of 8 mm, a length of 20 mm, and a thickness of 0.2 mm.

A stent was produced by coating the inner periphery and the outer periphery of the metallic stent matrix 10 with segmented polyurethane polymer films. As described concretely, a mandrel having a diameter of 3.8 mm and made of stainless steel was impregnated into a polyurethane solution, was then pulled up, and was dried so as to form a cylindrical coating of the polyurethane having 30 μm. The metallic stent matrix which was slightly expanded was overlaid on the coating with significant pressure. The mandrel with the stent matrix was impregnated into the polyurethane solution, was then pulled up, and was dried so as to form a coating having a thickness of 50 μm so that the inner and outer peripheries of the stent matrix were coated. After laser machining, the portions of the films protruding from the both ends were cut out. The mandrel with the stent was impregnated into methanol for 12 hours and the stent was pulled out from the mandrel.

The polyurethane solution was prepared by dissolving 10% by weight of segmented polyurethane, a trade name Capdiomat, (available from Kontoron Cardiovascular Inc.) into a mixed solution of tetrahydrofuran and dioxane.

The speed of pulling up the mandrel was lowered in a linear fashion such that the initial speed was 10 mm/minute and the last speed was 5 mm/minute. Sections cut in the radial direction by high stainless steel were taken by a microscope. As a result of measuring the thickness of the film at the sections, the thickness of the film at a section corresponding to an upper end of the mandrel during impregnation was 78.6 μm±4.3 μm and the thickness at a section corresponding to a lower end of the mandrel was 80.1 μm±2.4 μm. From this result, it was found that the film thus formed had a substantially uniform thickness.

The films were perforated by excimer laser to have pores having a diameter of 100 μm such that the pores were substantially equally arranged at intervals of 200 μm. Pores aligned along 24 lines in total were formed by repeating a process of turning the cylindrical polymer film at 15° in the circumferential direction after forming pores in a line in the longitudinal direction.

Comparative Example 3

A stent was produced in the same manner as Example 4 except that the speed of pulling up the mandrel was constant at 10 mm/minute. As a result of measuring the thickness of the film at radial sections in the same manner as Example 4, the thickness of the film at a section corresponding to an upper end of the mandrel during impregnation was 77.1 μm±3.1 μm and the thickness of the film at a section corresponding to a lower end of the mandrel was 89.3 μm±4.2 μm. From this result, it was found that thickness of the film thus formed was different in the vertical positional relationship. From this, it was noted that the thickness of the polymer film according to the present invention is uniform.

The metallic stent provided with polymer film covering of the third invention can prevent adverse effects to human tissues such as thrombus due to metal. Particularly, since the polymer films are attached to the inner periphery and the outer periphery of the stent matrix, excellent biocompatibility can be given to the stent. The present invention can achieve homogenization of thickness of the polymer film.

(IV) Explanation of Fourth Invention

The dimension, configuration, and material of a stent matrix employed in a process of producing a stent of the fourth invention are the same as those of the suitable stent matrix of the first invention.

As for the material and thickness of a flexible polymer film, fine pores, biodegradable polymers to be coated on the outer periphery of an outer polymer film and on the inner periphery of an inner polymer film, methods of forming these coatings, therapeutic drugs to be contained in the biodegradable polymers, and a lubricative substance to be coated on the outer surface of the outer polymer film, the same description about the flexible polymer layer in the first invention can be adopted to this invention.

In the process of producing a stent of the fourth invention, a tubular polymer film for inner layer is fitted into a stent matrix and a tubular polymer film for outer layer is overlaid onto the stent matrix. After that, the respective polymer films are welded to the stent matrix.

For welding the polymer films, heat is applied to the stent matrix and the polymer films. As means of applying heat, a method of heating them from outside or a method of high-frequency dielectric heating may be employed. In addition, when the stent matrix is made of a conductive material such as a metal, a method of heating them with Joule heat caused by applying current or high-frequency induction current or a method of heating them with frictional heat caused by supersonic vibration may be employed.

During the welding, it is preferable to apply pressure onto the stent matrix and the respective films from both sides. For conducting this pressurization, it is preferable that a mandrel is inserted into the tubular polymer film for inner layer and pressure is applied to the polymer film for outer layer in radial direction toward the middle line. In addition, a method of applying pressure by using a heat shrinkable film may be employed.

To apply pressure, a method of pressing a cylindrical pressurizing device may be employed. Preferably a method of applying pressures of an pressure medium such as liquid (for example, oil and water) or gas (for example, air, nitrogen, and argon) onto the inner and outer peripheries of the polymer films is employed. An example of such a method is hot isostatic pressing.

In case of conducting the heating and pressurization in a state that the mandrel is inserted into the stent matrix to which the polymer film for inner layer and the polymer film for outer layer made of a segmented polyurethane polymer are attached and the ends of the polymer films are attached closely not to allow invasion of heating medium, the suitable temperature is about 100-300° C., the suitable pressure is about 1-20 MPa, and the suitable heating and pressurizing time period is about 0.5-10 minutes.

Fine pores are formed in the stent intermediate which comprises the stent matrix and the polymer films attached to both the inner and outer peripheries of the stent matrix in the aforementioned manner.

In the fourth invention, in case of containing a therapeutic drug into the coating layer of the biodegradable polymer, it is preferable to add the therapeutic drug to the biodegradable polymer solution. By adjusting the kind and the molecular weight of the biodegradable polymer and the thickness of the coating, the time and the period when the therapeutic drug is discharged into the body can be controlled. In case of forming a coating layer of a biodegradable polymer or a lubricative polymer, fine pores are formed by laser machining after the formation of the coating layer.

In the fourth invention, one stent may be composed of two or more stent matrixes which are arranged coaxially and slightly spaced apart from each other. In such a stent, a portion between the stent matrixes can be flexibly bent.

Example 5

As the stent matrix, a mesh stent matrix 10 having an inner diameter of 3.1 mm, an outer diameter of 3.2 mm, and a length of 20 mm shown in FIG. 2 was employed.

FIG. 3 is a perspective view of the metallic stent matrix 10' after being expanded. The metallic stent matrix 10' in this state has an outer diameter of 8 mm and a length of 20 mm.

As the polymer film for inner layer, a tubular film made of a segmented polyurethane polymer and having an inner diameter of 2.9 mm, an outer diameter of 3.1 mm, and a length of 40 mm was employed. As the polymer film for outer layer, a tubular film made of a segmented polyurethane polymer and having an inner diameter of 3.2 mm, an outer diameter of 3.4 mm, and a length of 40 mm was employed.

The polymer film for inner layer was fitted into the stent matrix and the polymer film for outer layer is overlaid onto the stent matrix. Further, a mandrel having a diameter of 2.9 mm is fitted into the polymer film for inner layer. Then, the stent matrix together with the mandrel is mounted into a lower mold half having a semi-cylindrical inner bore and an upper mold half having a semi-cylindrical inner bore was put over them. They were heated and pressurized for 2 minutes at a temperature of 160° C. and a pressure of 2 MPa, thereby forming an integrated body. The body was released from the mold halves and was processed by laser machining, thus forming a stent.

As the laser maching, excimer laser was employed to form pores having a diameter of 100 μm such that the pores were substantially equally arranged at intervals of 200 μm. Pores aligned along 24 lines in total were formed by repeating a process of turning the cylindrical polymer film at 15° in the circumferential direction after forming pores in a line in the longitudinal direction.

Example 6

Instead of the pressurization and heating using the mold, polymer films were welded to the stent matrix with pressure by hot isostatic pressing. That is, polymer films are attached to the stent matrix such that ends of the inner and outer polymer films were welded by heat not to allow a heating medium to invade between the inner film and the outer film. The stent matrix with the polymer films was put into a pressure vessel filled with oil as the medium and was heated and pressurized for 3 minutes at 160° C. and 10 MPa, thereby bonding the polymer films to the inner periphery and the outer periphery of the stent matrix. Except the above, the stent was produced in the same manner as Example 5.

Each of the stents of the respective examples was grafted in a carotid artery of a rabbit. Observation was conducted after one month. As a result, it was observed that the intimal thickening was thin and the formation of thrombus was prevented.

The stent produced according to the process of the fourth invention can prevent adverse effects to human tissues such as thrombus due to metal. Particularly, since the polymer films are attached to the inner periphery and the outer periphery of the stent matrix, excellent biocompatibility can be given to the stent.

(V) Explanation of Fifth Invention

Figure 15:
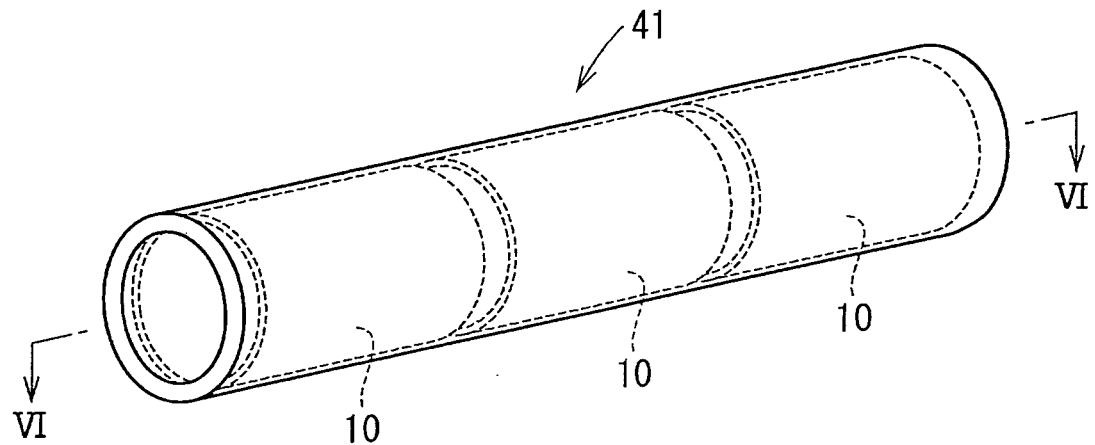
FIG. 15 is a schematic perspective view of a stent according to an embodiment of the fifth invention.
Figure 16A:
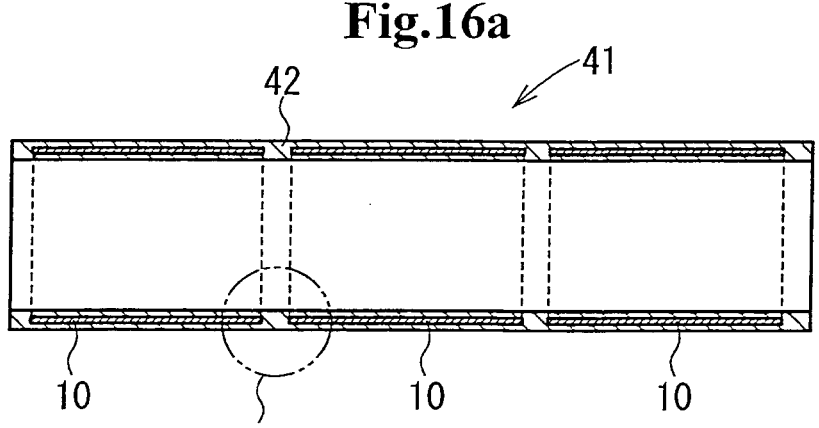
FIG. 16a is a sectional view taken along a line VI-VI of FIG. 15
Figure 16B:
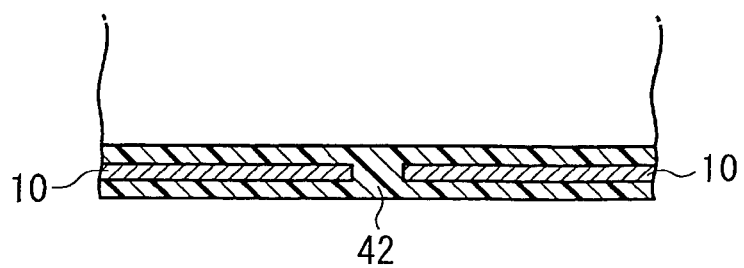

FIGS. 15, 16a, and 16b are explanatory views of a stent of the fifth invention. It should be understood that FIGS. 15, 16a, and 16b are schematic views so that particularly the thickness is shown larger than the actual thickness.

As shown in FIGS. 15, 16a, and 16b, a stent 41 according to an embodiment of the fifth invention comprises a plurality of stent matrixes 10 which are aligned coaxially and of which inner and outer peripheries are both coated by a polymer film 42 so that the stent matrixes are united by the polymer film 42.

The dimension, configuration, and material of each stent matrix employed in the stent of the fifth invention are the same as those of the suitable stent matrix of the first invention.

In the fifth invention, the stent matrixes are aligned in the longitudinal direction thereof and the number of the stent matrixes is preferably from 2 to 10, especially preferably from 2 to 5. The interval formed between adjacent stent matrixes is preferably from about 0.1% to 1000%, more preferably from 1% to 500%, especially preferably from 1% to 100% of the diameter of each stent matrix.

It is preferable that the stent matrixes are independent from each other and are connected to each other by only the coating polymer film. However, adjacent stent matrixes may be connected to each other by a wire made of the same material of that of the stent matrix such that the wire extends from a single point on the circumference of the end of one stent matrix to a single point on the circumference of the end of the other stent matrix. Even when the respective single points on the circumferences are connected to each other, the bendability of the stent is little affected. The wire connecting the stent matrixes increases the tensile strength in the longitudinal direction of the stent. On the other hand, when the wire is not used, the bendability of the stent is significantly high.

The stent matrixes are preferably aligned coaxially with high accuracy and are connected by the flexible polymer film attached to the inner and outer peripheries thereof so that the stent matrixes form a continuous cylinder. The polymer film is cylindrical even at connecting parts between the stent matrixes. Both on the inner periphery and the outer periphery of the stent 41, the polymer film 42 is continued from one end to the other end of the stent 41.

As for the material and thickness of the flexible polymer films, fine pores, biodegradable polymers to be coated on the outer periphery of an outer polymer film and on the inner periphery of an inner polymer film, methods of forming these coatings, therapeutic drugs to be contained in the biodegradable polymers, and a lubricative substance to be coated on the outer surface of the outer polymer film of the fifth invention, the same description about the flexible polymer layer in the first invention can be adopted to this invention.

Also in the fifth invention, fine pores of the polymer films are preferably formed by laser or the like after the polymer film is attached to the inner and outer peripheries of the stent matrixes.

In the fifth invention, a coating layer of a biodegradable polymer can be formed by impregnating the stent into a biodegradable polymer solution. Polymerization may be promoted by ultraviolet ray after pulling up the stent from the polymer solution. In case of forming the polymer films by the centrifugal molding method according to the second invention, the biodegradable polymer coating layer may also be formed by the centrifugal molding method. By adding a therapeutic drug into the biodegradable polymer solution, a coating containing the therapeutic drug is formed. By adjusting the kind and the molecular weight of the biodegradable polymer and the thickness of the coating, the time and period when the therapeutic drug is discharged into the body can be controlled.

For producing the stent of the fifth invention, according to the process of the aforementioned third invention, a mandrel is impregnated into a polymer solution of polyurethane or the like to form a cylindrical coating of the polymer on the mandrel, the metallic stent matrixes which are slightly expanded were overlaid on the coating with significant pressure, and they are further impregnated into the polymer solution to form coating, thereby forming a film coating both peripheries of the stent matrixes. After the film is processed by laser machining, portions protruding from the both ends are cut. Then, the stent is pulled out from the mandrel.

The outer peripheries and the inner peripheries of the stent matrixes may be covered by cylindrical cover strips of which one ends are closed. To attach the cover strip to the outer peripheries of the stent matrixes, the stent matrixes are inserted into the cover strip in a state that the cover strip is sufficiently opened by sending air into the cover strip and the sending of air is stopped to shrink the cover strip so that the cover strip is closely attached to the outer peripheries of the stent matrixes. To attach the cover strip to the inner peripheries of the stent matrixes, the cover strip is inserted into the stent matrixes and air is supplied into the cover strip to expand the cover strip so that the cover strip is closely attached to the inner peripheries of the stent matrixes. Portions protruding from the stent matrixes are preferably cut.

The stent of the fifth invention can be also made by the centrifugal molding method according to the second invention.

That is, while a cylindrical mold is rotated rapidly about its axis, a liquid resin material for forming polymer film is supplied into the mold, thereby forming a polymer film for outer layer. The liquid resin material may be solution of a polymer or a polymerizable liquid resin material of a monomer or the like. After the polymer film for outer layer is subjected to hardening treatment such as drying or ultraviolet irradiation if necessary, a plurality of stent matrixes are inserted into the mold such that the stent matrixes are arranged coaxially with the polymer film for outer layer. Then, the mold is rotated rapidly, a liquid resin material for forming a polymer film for inner layer is supplied into the mold, thereby forming a polymer film for inner layer. After the polymer film for inner layer is subjected to hardening treatment such as drying or ultraviolet irradiation, the mold is removed, thereby producing a stent.

Example 7

As each stent matrix, a mesh stent matrix 10 having a diameter of 4 mm, a length of 13 mm, and a thickness of 0.2 mm shown in FIG. 2 was employed.

FIG. 3 is a perspective view of the metallic stent matrix 10' after being expanded. The metallic stent matrix 10' in this state has a diameter of 8 mm, a length of 13 mm, and a thickness of 0.2 mm.

A stent was produced by coating the inner peripheries and the outer peripheries of three metallic stent matrixes 10 with a segmented polyurethane polymer film 42. As described concretely, a mandrel was impregnated into a polyurethane solution so as to form a cylindrical coating on the mandrel. The three stent matrixes which were slightly expanded were overlaid on the coating with significant pressure such that the stent matrixes are spaced apart from each other by 2 mm. The mandrel with the stent matrixes was further impregnated into the polyurethane solution so as to form a coating so that both the inner and outer peripheries of the stent matrixes were coated. After fine pores were formed in the polymer film by laser machining, the portions of the film protruding from the both ends were cut out. The mandrel with the stent was impregnated into methanol and the stent was pulled out from the mandrel. In this manner, a cylindrical member (stent intermediate) in which the polymer film on the inner periphery was 30 μm in thickness and the polymer film on the outer periphery was 50 μm in thickness was obtained.

The polyurethane solution was prepared by dissolving 10% by weight of segmented polyurethane, a trade name Capdiomat, (available from Kontoron Cardiovascular Inc.) into a mixed solution of tetrahydrofuran and dioxane.

The stent intermediate was perforated by excimer laser to have pores having a diameter of 100 μm such that the pores were substantially equally arranged at intervals of 200 μm. Pores aligned along 24 lines in total were formed by repeating a process of turning the cylindrical polymer film at 15° in the circumferential direction after forming pores in a line in the longitudinal direction.

Comparative Example 4

A stent was produced in the same manner as Example 7 except that only one stent matrix having a length of 40 mm was used.

The stents of Example 7 and Comparative Example 4 were laid horizontally. One end of each stent was fixed and a load of 5 g was applied downwardly to the other end. As a result, the displacement of Example 7 was 5 mm, while the displacement of Comparative Example 4 was 0 mm.

The stent was grafted in a carotid artery of a rabbit. Observation was conducted after one month. As a result, it was observed that the intimal thickening was thin and the formation of thrombus was prevented.

The metallic stent provided both on the inner and outer peripheries with the polymer film covers of the fifth invention can be flexibly bent and can prevent adverse effects to human tissues such as thrombus due to metal.

(VI) Explanation of Sixth Invention

In the aforementioned fifth invention, a plurality of stent matrixes 10 are preferably aligned coaxially with high accuracy and are connected by the flexible polymer film 42 attached to the inner and outer peripheries thereof so that the stent matrixes form a continuous cylinder, as shown in FIGS. 15, 16a, and 16b. The polymer film 42 is cylindrical even at connecting parts between the stent matrixes. Both on the inner periphery and the outer periphery of the stent 41, the polymer film 42 is continued from one end to the other end of the stent 41.

Since the stent 41 is composed of a plurality of stent matrixes 10 and can be flexibly bent at portions between the stent matrixes 10 and 10, the stent can be easily passed through even a vascular channel which is bent. However, the stent has the following problem.

That is, since the both the outer and inner peripheries of the stent matrixes are coated by the flexible polymer film such that the flexible polymer film is completely closely attached to these peripheries in the stent of the fifth invention, the polymer film may be twisted during the expansion of the stent matrixes, thus causing a problem of being wrinkled and/or being torn. In case of a stent in which stent matrixes which are geometrically deformable during radial expansion and the deformation of the respective stent matrixes are complex or the degree of the deformation is large, this problem becomes significant.

The sixth invention was made in order to solve this problem.

Figure 17A:
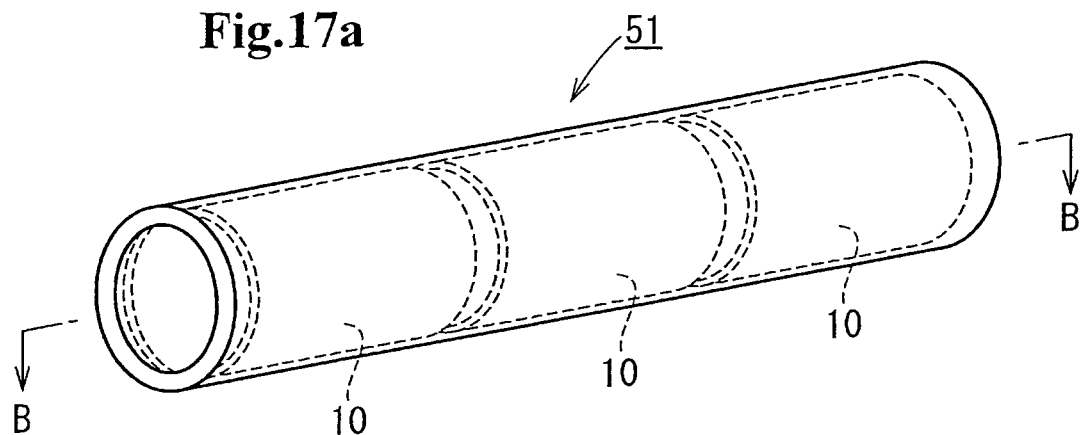
FIG. 17a is a perspective view showing an embodiment of a stent of the sixth invention.
Figure 17B:
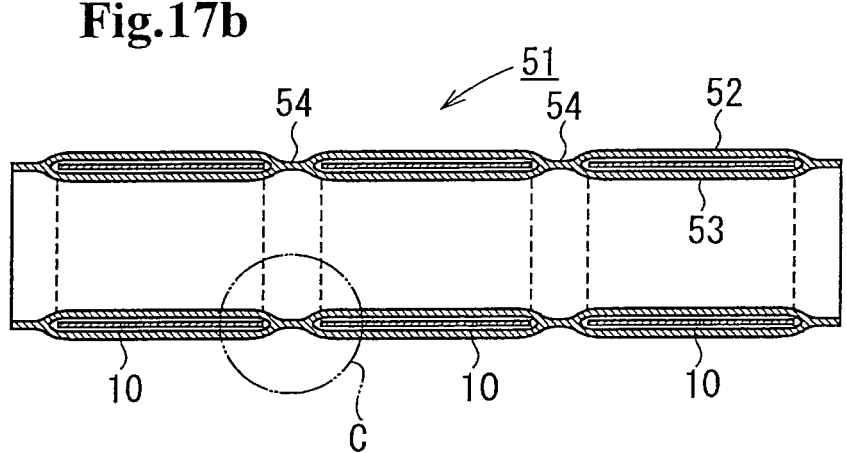
FIG. 17b is a sectional view taken along a line B-B of FIG. 17a, and FIG. 17c is an enlarged view of a portion C of FIG. 17b.
Figure 17C:
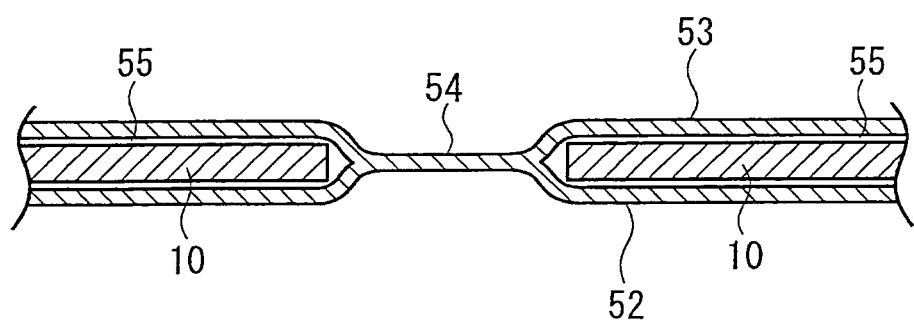

FIG. 17a is a perspective view showing an embodiment of the stent of the sixth invention, FIG. 17b is a sectional view taken along a B-B of FIG. 17a, and FIG. 17c is an enlarged view of a portion C of FIG. 17b. FIGS. 17b and 17c are schematic views so that particularly the thickness is shown larger than the actual thickness.

As shown in FIGS. 17a-17c, a stent 51 according to an embodiment of the sixth invention comprises a plurality of stent matrixes 10 of which diameter is extendable and which are aligned coaxially and of which inner and outer peripheries are both coated by an outer polymer film 52 and an inner polymer film 53 so that the stent matrixes are united by the polymer films 52, 53.

The dimension, configuration, and material of each stent matrix employed in the stent of the sixth invention are the same as those of the suitable stent matrix of the first invention.

The number of the stent matrixes and the interval between adjacent stent matrixes are the same as those of the fifth invention.

As for the material and thickness of the flexible polymer films, fine pores, biodegradable polymers to be coated on the outer periphery of an outer polymer film and on the inner periphery of an inner polymer film, methods of forming these coatings, therapeutic drugs to be contained in the biodegradable polymers, and a lubricative substance to be coated on the outer surface of the outer polymer film, the same description about the flexible polymer layer in the first invention can be adopted to this invention.

In the stent of the sixth invention, the stent matrixes can move between the outer polymer film and the inner polymer film as described in the above. Since the stent is therefore excellent in bendability and deformation following property, the entire shape of all of the stent matrixes is not necessarily straight tubular. One or more of the stent matrixes may be a bent tube which is bent in a substantially L-shape or a substantially V-shape. That is, a surgeon can select the shape suitable for the shape of a blood vessel to which the stent will be grafted.

The stent matrixes are preferably aligned coaxially with high accuracy and the inner and outer peripheries of the stent matrixes are coated with flexible polymer films so that the stent matrixes form a continuous cylinder. The polymer films are cylindrical even at connecting parts between the stent matrixes. Both on the inner periphery and the outer periphery of the stent 51, the polymer films are continued from one end to the other end of the stent 51.

In the stent 51 shown in FIGS. 17a-17c, the outer polymer film 52 and the inner polymer film 53 are not bonded to the stent matrixes so that the outer polymer film 52 and the inner polymer film 53 can shift relative to the stent materials 10 during the expansion of the stent matrixes 10. The outer polymer film 52 and the inner polymer film 53 are bonded to each other only at portions between adjacent stent matrixes 10, 10 and at both ends thereof where no stent matrix exists. In FIGS. 17b and 17c, a numeral 54 designates the bonded portion of the polymer films 52 and 53.

The stent 51 in which the outer polymer film 52 and the inner polymer film 53 are not bonded to the stent matrixes 10 and are bonded to each other only at portions between adjacent stent matrixes 10, 10 and at both ends thereof can be produced by a process suitable for producing this stent as an application of the aforementioned process of the fourth invention. That is, the process comprises: sandwiching a plurality of stent matrixes between two tubular polymer films and heat-sealing the outer polymer film 52 and the inner polymer film 53 to each other only at the portions between adjacent stent matrixes 10, 10 and the both ends thereof in the mold.

Fine pores of the polymer films may be formed by laser or the like after the stent matrixes are coated with the outer polymer film and the inner polymer film.

Space 55 between each stent matrix and the outer polymer film 52 and the inner polymer film 53 may be just airspace and may be filled with therapeutic drug or other filler. In case of airspace, this portion is inflated with air, thereby preventing the adhesion between the polymer films 52 and 53.

In case of filling a therapeutic drug, examples of fillers include aqueous solution such as normal saline solution containing heparin, low-molecular heparin, hirudin, argatroban, formacolin, vapiprost, prostamoline, prostakilin homolog, dextran, D-phe-pro-arg chloromethyl ketone, dipyridamole, platelet receptor antagonist of glycoprotein, recombinant hirudin, thrombin inhibitor, vascular heptyne, angiotensin-converting enzyme inhibitor, steroid, fibrocyte growth factor antagonist, fish oil, omega 3 fatty acid, histamine, antagonist, HMG-CoA reductase inhibitor, seramin, serotonin blocker, thioprotease inhibitor, triazolopyrimidine, interferon, vascular endothelial growth factor (VEGF), rapamycin, FK506, solution of hydrophilic solvent such as glycerin, ethylene glycol, or alcohol, atactic PP, EVA, low-molecular PE, silicone oil, gelatine, collagen, hyaluronic acid, and pullulan. These fillers may have sustained-release property that is a property of gradually releasing through the fine pores. A radioactive substance, magnetic powder, or the like may be used as a filler. In this case, in a therapy for a cancerous part of vascular channel, the radioactive substance can inhibit cancer progression by radioactive ray and the magnetic powder can provide hyperthermia for cancer by electromagnetic induction heating. The magnetic powder effects in a therapy for narrowed blood vessel after the stent is grafted by inhibiting excessive growth of smooth muscle cells since a diseased part can be stimulated by electromagnetic induction cased by application of magnetic force from outside of the body so as to transformation and/or differentiation-induction of smooth muscle cells in the blood vessel from synthetic type to contraction type. The heat generation, vibration, and weak current treatments of the stent by such electromagnetic induction can be said to be non-invasive catamnestic management methods.

The space between the outer polymer film and the inner polymer film can be filled with such a filler by the following method. That is, in the production of the stent according to the aforementioned example method, the stent matrixes are sandwiched between two tubular polymer films and the outer polymer film 52 and the inner polymer film 53 are heat-sealed to each other only at one end on a side of the stent matrix 10 positioned at the rearmost end so as to form an envelope-like pocket portion. The filler is injected into the pocket portion and the outer polymer film 52 and the inner polymer film 53 are heat-sealed to each other at a portion between adjacent stent matrixes 10. This operation consisting of injection of the filler and the heat sealing is repeated sequentially, thereby filling the space between the outer polymer film and the inner polymer film with the filler. It is possible to change the kind of filler for every envelope-like pocket portion so as to use several kinds of fillers.

In the stent of the sixth invention, the outer polymer film and the inner polymer film may be bonded partially to the stent matrix without disturbing the shift between the polymer film and the stent matrix during the expansion of the stent matrix. In this case, for example, dot-like bonded portions of about from 1 μm to 1000 μm in diameter may be provided at scattered positions. By partially bonding the polymer film to the stent matrix, the expansion following property of the inner polymer film during the expansion of the stent is increased.

For providing the dot-like bonded portions, for example, a method comprising: previously putting photo-curing resin into portions to be bonded between the outer polymer film and inner polymer film and the stent matrix; and curing the photo-curing resin by irradiation of laser light which is throttled to have a light diameter equal to the diameter of the dot-like bonded portions may be employed.

In addition, the bonded portions thus formed may be perforated by laser. For example, a pore about 30 μm in diameter may be formed at substantially the center of the dot-like bonded portion of 50 μm in diameter. By providing such pores, the growth of endothelial cells can be promoted.

In the stent of the sixth invention, the outer polymer film and the inner polymer film may be bonded partially to each other at meshes of the mesh stent matrix without disturbing the shift between the polymer film and the stent matrix during the expansion of the stent matrix. In this case, for example, dot-like bonded portions of about from 1 μm to 1000 μm in diameter may be provided at meshes of the mesh stent matrix, i.e. stent slots. Also by partially bonding the outer and inner polymer films to each other at stent slots to have dot-like bonded portions (pinpoint bonding), the expansion following property of the inner polymer film during the expansion of the stent is increased.

Also in case of providing the dot-like bonded portions at the stent slots, for example, a method comprising: putting photo-curing resin to portions to be bonded between the outer polymer film and inner polymer film; and curing the photo-curing resin by irradiation of laser light which is throttled to have a light diameter equal to the diameter of the dot-like bonded portions may be employed, just like the aforementioned case. Alternatively, a method comprising: mounting stent matrixes with outer and inner polymer films onto a mandrel; and heating and pressing the mandrel by a heat roller, which is provided with a plurality of pins formed on the outer periphery thereof, so as to weld the outer and inner polymer films to each other in the dot-like form at the stent slots may be employed.

In addition, the bonded portions thus formed may be perforated by laser. For example, a pore about 30 μm in diameter may be formed at substantially the center of the dot-like bonded portion of 50 μm in diameter. By providing such pores, the growth of endothelial cells can be promoted as mentioned above.

Example 8

As each stent matrix, a mesh stent matrix 10 having a diameter of 4 mm, a length of 7 mm, and a thickness of 0.1 mm shown in FIG. 2 was employed. FIG. 3 is a perspective view of the metallic stent matrix 10' after being expanded. The metallic stent matrix 10' in this state has a diameter of 8 mm, a length of 7 mm, and a thickness of 0.1 mm.

A stent was produced by coating the inner peripheries and the outer peripheries of three metallic stent matrixes 10 with segmented polyurethane polymer films.

As described concretely, a tube having an outer diameter of 3.8 mm and made of thermoplastic polyurethane resin (MIRACTRAN E980; available from Nippon Miractran Co., Ltd.) was overlaid on a mandrel in which SUS440 portions having an outer diameter of 3.5 mm and a length of 1 mm and PTFE portions having a length of 7 mm were alternately arranged without irregularities and were kept in a refrigerator at 4° C. Three stent matrixes 10 were aligned with intervals of about 1 mm and the mandrel with the resin tube was inserted into the stent matrixes 10.

Then, a tube having an outer diameter of 4.3 mm and made of thermoplastic polyurethane resin (MIRACTRAN E980; available from Nippon Miractran Co., Ltd.) was overlaid on a mandrel having an outer diameter of 4.1 mm and made of PTFE. The end of the mandrel with the tube was connected to the end of the aforementioned mandrel with the three stent matrixes and the resin tube such that the mandrels were arranged coaxially. The tube of 4.3 mm in outer diameter was slid from the mandrel to the other mandrel in methanol while applying ultrasonic waves, whereby the tube is overlaid to the three stent matrixes.

In this manner, in the order from the outside, the resin tube of 4.3 mm in outer diameter, the three stent matrixes, the resin tube of 3.8 mm in outer diameter, the mandrel in which the SUS440 portions of 3.5 mm in outer diameter and 1 mm in length and the PTFE portions of 7 mm in length are arranged alternately without irregularities were laminated. By using a mold having a structure capable of pressing the films at the portions between adjacent stent matrixes 10 and 10 and at both end portions in this state, the outer polymer film 52 and the inner polymer film were heat-sealed only at portions between adjacent stent matrixes 10 and 10 and at both end portions in the mold, thereby overlaying the outer polymer film on the outer peripheries of the stent matrixes and overlaying the inner polymer film on the inner peripheries of the stent matrixes. The interval between adjacent stent matrixes was set to 1.0 mm.

Comparative Example 5

A stent was produced in the same manner as Example 8 except the following. That is, a mesh stent matrix 10 having a diameter of 4 mm, a length of 25 mm, a thickness of 0.1 mm was employed as each stent matrix. A mold having an inner diameter of 4.1 mm and made of PTFE was rotated at 6000 rpm, a 10% THF solution of polyurethane resin was supplied into the mold while moving the injection position along the axial direction of the mold, and the solution was heated at 60° C., thereby forming a polymer film for outer layer having a thickness of 30 μm. Three stent matrixes were inserted into the mold such that the stent matrixes are arranged at intervals of 1 mm. The THF solution of polyurethane resin was supplied to form a film while rotating the mold in the same manner. Therefore, the outer polymer film and the inner polymer film around the stent matrixes were bonded entirely. The thickness of the polymer film for inner layer was 30 μm.

As the stents produced in Example 8 and Comparative Example 5 were expanded, it was found that the stent of Example 8 can be expanded comfortably without twisting nor wrinkling the polymer films because the stent matrixes moved slidably between the polymer films, while the stent of Comparative Example 5 can not stand the expansion, large deformation, and bending of the stent because the polymer films and the stent matrixes are completely closely attached to each other so that the polymer film is twisted and wrinkled.

The sixth invention can provide a stent of which outer and inner peripheries are coated with polymer films so as to reduce formation of thrombus and which can be flexibly bent and thus flexibly follow any deformation and expansion of stent matrixes.

(VII) Explanation of Seventh Invention

Figure 18A:
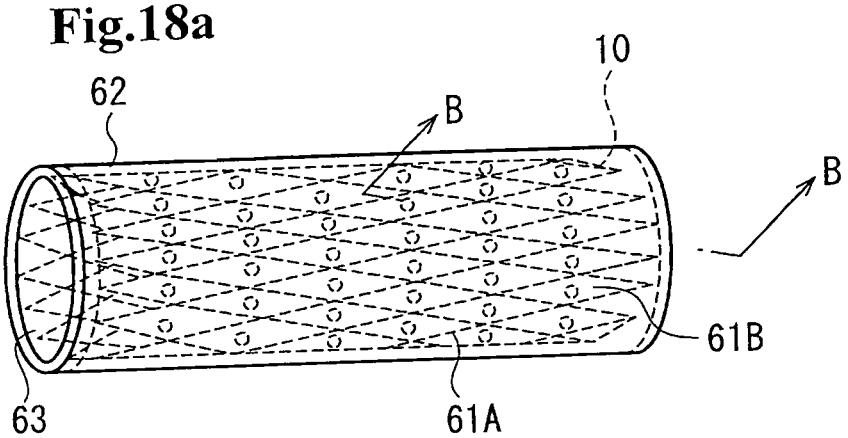
FIG. 18a is a perspective view showing an embodiment of a stent of the seventh invention.
Figure 18B:
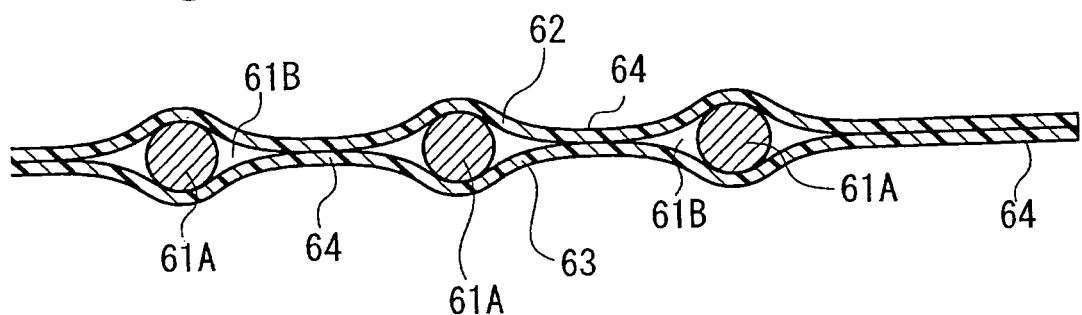
FIG. 18b is a sectional view taken along a line B-B of FIG. 18a, and FIG. 18c is a sectional view showing another embodiment.
Figure 18C:
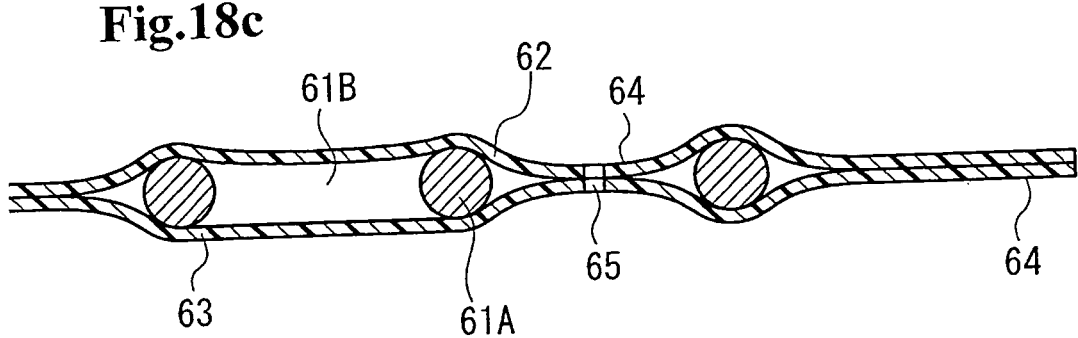

FIG. 18a is a perspective view showing an embodiment of the stent of the seventh invention, FIG. 18b is a sectional view taken along a B-B of FIG. 18a, and FIG. 18c is a sectional view showing another embodiment.

As shown in FIGS. 18a-18c, a stent 61 according to an embodiment of this invention comprises a tubular mesh stent matrix 10 of which diameter is extendable and of which outer and inner peripheries are coated with an outer polymer film 62 and an inner polymer film 63.

The dimension, configuration, and material of the stent matrix employed in the stent of the seventh invention are the same as those of the suitable stent matrix of the first invention.

In the stent of the seventh invention, the stent matrix can shift between the outer polymer film and the inner polymer film. Since the stent is therefore excellent in deformation following property, the entire shape of the stent matrix is not necessarily straight tubular and may be a bent tube which is bent in a substantially L-shape or a substantially V-shape. That is, a surgeon can select the shape suitable for the shape of a blood vessel to which the stent will be grafted.

Though only one stent matrix 10 is coated with the polymer films 62, 63 so as to form the stent 61 in FIG. 18a, a plurality of stent matrixes, for example, from 2 to 10, preferably from 2 to 5 may be aligned in the longitudinal direction thereof such that the interval formed between adjacent stent matrixes is from about 0.1% to 1000%, preferably from 1% to 500%, of the diameter of each stent matrix and the stent matrixes are united by the outer polymer film and the inner polymer film.

In the stent 61 shown in FIGS. 18a and 18b, the outer polymer film 62 and the inner polymer film 63 are not bonded to the stent struts 61A (lattice portions of the stent matrix 10) forming the lattice of the stent matrix 10 and the outer polymer film 62 and the inner polymer film 63 are bonded to each other at stent slots 61B, i.e. meshes of the stent matrix 10. In FIG. 18a, small circles shown by dashed lines in the stent slots 61B are bonded portions 64. It should be noted that the inner polymer film 63 and the outer polymer film 62 are bonded to each other at portions on both the ends of the stent 61 where no stent matrix exists such that the bonded portion forms a band-like ring shape.

Each bonded portion 64 formed in the stent slot 61B is preferably a dot-like bonded portion having a diameter of from about 5 μm to 500 μm, particularly about 50 μm to 300 μm.

As for the material and thickness of the flexible polymer films of the outer polymer film 62 and the inner polymer film 63, fine pores, biodegradable polymers to be coated on the outer periphery of an outer polymer film and on the inner periphery of an inner polymer film, methods of forming these coatings, therapeutic drugs to be contained in the biodegradable polymers, and a lubricative substance to be coated on the outer surface of the outer polymer film, the same description about the flexible polymer layer in the first invention can be adopted to this invention.

The stent 61 in which the outer polymer film 62 and the inner polymer film 63 are not bonded to the stent matrix 10 and are bonded to each other in the dot-like form at the stent slots 61B and bonded in the band-like form at both ends thereof can be produced by a process suitable for producing this stent as an application of the aforementioned process of the fourth invention.

That is, the process comprises: sandwiching a stent matrix between two tubular polymer films and heat-sealing the outer polymer film 62 and the inner polymer film 63 to each other only at the both ends thereof. For providing the dot-like bonded portions, photo-curing resin is previously into portions to be dot-like bonded portions between the outer polymer film and inner polymer film, and the photo-curing resin is cured by irradiation of laser light which is throttled to have a light diameter equal to the diameter of the dot-like bonded portions, thereby bonding the polymer films. As an alternative process, a heat roller which is provided with a plurality of pins formed on the outer periphery thereof is used. That is, the stent matrix with the outer and inner polymer films is mounted onto a mandrel, and the mandrel is heated and pressed by the heat roller so as to heat-seal the outer and inner polymer films to each other in the dot-like form at the stent slots.

Fine pores of the polymer films may be formed by laser or the like after the stent matrixes are coated with the outer polymer film and the inner polymer film.

In the seventh invention, the bonded portions are not necessarily formed in all of the stent slots and may be formed in some of the stent slots 61B. For example, the bonded portions may be formed in one stent slot apart or two stent slots apart not to form bonded portions in both the adjacent stent slots. As described in the above, the bonded portions thus formed may be perforated by laser. By providing such pores, the engraftment of endothelium of the blood vessel can be promoted as described in the above. For forming such pores, for example, a pore about 30 μm in diameter may be formed at substantially the center of the dot-like bonded portion of 50 μm in diameter. Alternatively, double wave mixed laser consisting of a YAG laser having a wavelength of 1064 nm which is throttled to be 50 μm and a quadruple-frequency YAG laser having a wavelength of 266 nm which is throttled to be 30 μm is used during the formation of dot-like bonded portions of 50 μm in diameter, thereby conducting the bonding and perforating at one time.

FIG. 18c shows an embodiment in which bonded portions 64 are formed in some of stent slots 61B and fine pores 65 are formed in the bonded portions 64.

In the stent, non-bonded portions between the outer polymer film 62 and the inner polymer film 63 at the stent slots 61 of the stent matrix 10 may be just airspace and may be filled with therapeutic drug or other filler. In case of airspace, this portion is inflated with air, thereby preventing the adhesion between the polymer films 62 and 63.

In case of filling a therapeutic drug, examples of fillers are the same as those listed in the sixth invention and the same effects as described in the sixth invention can be obtained.

The space between the outer polymer film and the inner polymer film can be filled with such a filler by sandwiching the stent matrix between two tubular polymer films, heat-sealing the outer polymer film 62 and the inner polymer film 63 to each other only at one end thereof so as to form an envelope-like pocket portion, and injecting the filler into the pocket portion.

Example 9

As the stent matrix, a mesh stent matrix 10 having a diameter of 4 mm, a length of 7 mm, and a thickness of 0.1 mm shown in FIG. 2 was employed. FIG. 3 is a perspective view of the metallic stent matrix 10' after being expanded. The metallic stent matrix 10' in this state has a diameter of 8 mm, a length of 7 mm, and a thickness of 0.1 mm.

A stent was produced by coating the inner periphery and the outer periphery of a metallic stent matrix 10 with segmented polyurethane polymer films.

As described concretely, a tube having an outer diameter of 3.8 mm and made of thermoplastic polyurethane resin (MIRACTRAN E980; available from Nippon Miractran Co., Ltd.) was overlaid on a mandrel in which a PTFE portion having a length of 7 mm was disposed between SUS440 portions having an outer diameter of 3.5 mm and a length of 1 mm and was kept in a refrigerator at 4° C. The mandrel with the resin tube was inserted into a single stent matrix 10.

Then, a tube having an outer diameter of 4.3 mm and made of thermoplastic polyurethane resin (MIRACTRAN E980; available from Nippon Miractran Co., Ltd.) was overlaid on a mandrel having an outer diameter of 4.1 and made of PTFE. The end of the mandrel with the tube was connected to the end of the aforementioned mandrel with the stent matrix and the resin tube such that the mandrels were arranged coaxially. The tube of 4.3 mm in outer diameter was slid from the mandrel to the other mandrel in methanol while applying ultrasonic waves, whereby the tube is overlaid on the stent matrix.

In this manner, in the order from the outside, the resin tube of 4.3 mm in outer diameter, the stent matrix, the resin tube of 3.8 mm in outer diameter, the mandrel of 3.5 mm in outer diameter were laminated. By using a mold having a structure capable of pressing the films at both end portions in this state, the outer polymer film and the inner polymer film were heat-sealed only at both end portions in the mold.

A heat roller which was provided with a plurality of pins on the outer periphery thereof was used to press the mandrel on which the stent matrix was covered by the outer and inner polymer films, thereby heat-sealing the outer and inner polymer films to each other at the stent slots in the dot form. The diameter of the bonded portions was about 50 μm and the bonded portions were formed in all of the stent slots of the stent matrix.

Comparative Example 6

A stent was produced in the same manner as Example 9 except the following. That is, a mesh stent matrix 10 having a diameter of 4 mm, a length of 25 mm, a thickness of 0.1 mm was employed as the stent matrix. A mold having an inner diameter of 4.1 mm and made of PTFE was rotated at 6000 rpm, a 10% THF solution of polyurethane resin was supplied into the mold while moving the injection position along the axial direction of the mold, and the solution was heated at 60° C., thereby forming a polymer film for outer layer having a thickness of 30 μm. The stent matrix was inserted into the mold. The THF solution of polyurethane resin was supplied to form a film while rotating the mold in the same manner. Therefore, the outer polymer film and the inner polymer film around the stent matrix were bonded entirely. The thickness of the polymer film for inner layer was 30 μm.

As the stents produced in Example 9 and Comparative Example 6 were expanded, it was found that the stent of Example 9 can be expanded comfortably without twisting nor wrinkling the polymer films because the stent matrix moved slidably between the polymer films, while the stent of Comparative Example 6 can not stand the expansion, large deformation, and bending of the stent because the polymer films and the stent matrix are completely closely attached to each other so that the polymer films are twisted and wrinkled.

The seventh invention can provide a stent of which outer and inner peripheries are coated with polymer films so as to reduce formation of thrombus and which can be flexibly follow any deformation and expansion of stent matrix.

What is claimed is:

1. A process of producing a stent, comprising:
preparing a tubular stent matrix extendable in a diametric direction,
forming flexible solid polymer layers on said stent matrix to cover entire inner and outer surfaces of the stent matrix, and
perforating a plurality of fine through pores in the solid polymer layers at portions only where the stent matrix does not exist,
wherein said forming the solid polymer layers comprises a step of installing the stent matrix on an inner polymer layer disposed on an outer surface of a mandrel;
a step of forming an outer polymer layer by impregnating the mandrel into a liquid resin material for forming the outer polymer layer and pulling up the mandrel; and
a step of equalizing the thickness of the outer polymer layer by pulling up the mandrel in a vertical direction and controlling a pulling-up speed, and
wherein said fine pores are formed after the polymer layers are formed.

2. A process of producing a stent as claimed in claim 1, wherein the pulling-up speed is gradually lowered.

3. A process of producing a stent as claimed in claim 1, wherein the outer polymer layer is made of a base resin material only.

4. A process of producing a stent as claimed in claim 1, wherein the outer polymer layer comprises a base layer made of a base resin material and a layer of a biodegradable polymer covering the surface of the base layer.

5. A process of producing a stent as claimed in claim 3, wherein the liquid base resin material is a solution of segmented polyurethane polymer.

6. A process of producing a stent as claimed in claim 1, wherein said fine pores are formed by laser machining.

7. A process of producing a stent as claimed in claim 1, wherein said forming the solid polymer layers further comprises a step of impregnating the mandrel into a polymer liquid for the inner layer and pulling up the mandrel to form the inner polymer layer, on which the stent matrix is installed.

* * * * *